(12) United States Patent
Fujita et al.

(10) Patent No.: US 8,650,933 B2
(45) Date of Patent: Feb. 18, 2014

(54) GAS SENSOR

(75) Inventors: Yasuhiro Fujita, Kaizu (JP); Takayoshi Atsumi, Konan (JP)

(73) Assignee: NGK Spark Plug Co. Ltd., Aichi (JP)

( * ) Notice: Subject to any disclaimer, the term of this patent is extended or adjusted under 35 U.S.C. 154(b) by 301 days.

(21) Appl. No.: 13/078,401

(22) Filed: Apr. 1, 2011

(65) Prior Publication Data
US 2011/0239740 A1 Oct. 6, 2011

(30) Foreign Application Priority Data
Apr. 2, 2010 (JP) .................................. 2010-085762

(51) Int. Cl.
*G01N 7/00* (2006.01)

(52) U.S. Cl.
USPC ........................................................ 73/31.07

(58) Field of Classification Search
USPC .......................... 73/23.2, 31.05, 31.07, 23.31; 204/424–428
See application file for complete search history.

(56) References Cited

U.S. PATENT DOCUMENTS 7,870,777 B2    1/2011  Fujii et al. .................... 73/31.05

FOREIGN PATENT DOCUMENTS

| JP | 2008-292459 A | 12/2008 |
| JP | 2008-292460 A | 12/2008 |
| JP | 2008292459 A * | 12/2008 |

* cited by examiner

*Primary Examiner* — Peter Macchiarolo
*Assistant Examiner* — Tamiko Bellamy
(74) *Attorney, Agent, or Firm* — Sughrue Mion, PLLC

(57) ABSTRACT

A gas sensor, including a cylindrical outer tube; and a seal member disposed in the outer tube, the seal member including: a lead wire insert hole and an atmosphere communication hole extending in an axial direction thereof. The gas sensor further includes: a protection portion which covers the atmosphere communication hole from the rear end of the gas sensor in the axial direction, the protection portion having a protrusion which protrudes toward a rear side of the gas sensor, and has an opening smaller than an opening of the atmosphere communication hole, wherein the protrusion is disposed at a further front end side of the rear end surface of the seal member.

6 Claims, 15 Drawing Sheets

GAS SENSOR

BACKGROUND OF THE INVENTION

1. Field of the Invention

The present invention relates to a gas sensor, which holds a sensor element for measuring a gas to be measured in a metal shell or an outer tube, and has a ventilation structure for ensuring ventilation between the inside and the outside of the outer tube.

2. Description of the Related Art

A gas sensor having a sensor element for detecting the concentration of a specific gas component (e.g., oxygen) in an exhaust gas discharged from an engine using a solid electrolyte body containing a ceramic such as zirconia is well-known in the art. For example, a sensor element of an oxygen sensor for detecting the concentration of oxygen includes a detection electrode exposed to the exhaust gas and a reference electrode exposed to a reference gas (commonly, the atmosphere). The electrodes are formed on an outer or inner surface of the sensor element, and are paired with a counter electrode on opposing sides of a solid electrolyte body. The sensor element detects the concentration of oxygen in the exhaust gas in accordance with the difference in partial pressure of oxygen between two atmospheres spaced apart from the solid electrolyte body, namely between the exhaust gas and the reference gas.

This oxygen sensor includes a metal shell for holding the sensor element, and an outer tube for covering the periphery of the sensor element, and a seal member (grommet) may be assembled thereto to block the outer tube. In addition, the seal member has a lead wire insert hole for inserting a lead wire (a sensor output lead wire and a heater lead wire), and an atmosphere communication hole (or, a cylindrical hole) for introducing the reference gas toward the reference electrode of the sensor element by ensuring ventilation between the inside and the outside of the outer tube. Also, a filter member for introducing the atmosphere into the outer tube (air ventilation) and preventing the entry of water droplets (waterproofing properties) is provided in the atmosphere communication hole of the plug member.

In addition, as disclosed in the Patent Document 1 or 2, a gas sensor having a protection member for covering the atmosphere communication hole of the seal member from a rear side (an outer side) of the outer tube to protect the filter member is already known. Providing the protection member as mentioned above prevents the filter member from being directly exposed to the outside and also prevents the filter member from being damaged due to an impact from the outside, caused by contact with plants or trees or a collision with a flying stone. This protection member has a ventilation portion with a smaller opening than the atmosphere communication hole, and the ventilation portion cover the filter member. Also, the protection member has a covering portion, which is outside the line of sight and communicates with the atmosphere communication hole from the gap with the seal member. The protection member is connected to the outer tube by means of an arm.

Patent Document 1 JP-A-2008-292459
Patent Document 2 JP-A-2008-292460

3. Problems to be Solved by the Invention

However, among the protection members of a gas sensor disclosed in the Patent Documents 1 and 2, the protection member (see FIG. 14 of the Patent Document 2) having a plurality of small openings through the ventilation unit in an axial direction has a problem in that the openings may be clogged since each opening is too small.

Meanwhile, if a protrusion (see FIGS. 3 and 5 of Patent Document 1 and FIG. 12 of Patent Document 2) having an opening and protruding toward a rear end (an outer side) with a dome shape is provided on the ventilation unit, and the opening of the protrusion of the protection member communicates with the atmosphere communication hole by the protection member, then the opening is not easily clogged and good air ventilation can be ensured. However, if the protrusion protrudes from the rear end (the outer side) further than the rear end of the seal member when the protection member having the protrusion is disposed on the seal member to cover the filter member, a lead wire may be hooked by the edge of the protrusion when being installed, leading to a concern that damage to the lead wire may result.

SUMMARY OF THE INVENTION

The present invention was made to solve the above problems, and an object thereof is to provide a gas sensor capable of preventing a lead wire from being damaged when a seal member is disposed on a ventilation unit having a protrusion to cover a filter member.

According to an illustrative aspect (1), the above object of the present invention has been achieved by providing a gas sensor, comprising: a sensor element extending in an axial direction and having a detection portion for detecting a gas to be detected at a front end thereof; a metal shell that surrounds a periphery of the sensor element in a radial direction while allowing the detection portion to protrude from a front end thereof; a cylindrical outer tube disposed at a rear side of the metal shell and having a front end fixed to the metal shell; and a seal member disposed in the outer tube, the seal member including: a lead wire insert hole into which a lead wire for extracting a detection signal of the detector is inserted, the lead wire insert hole extending in an axial direction thereof, and an atmosphere communication hole allowing atmospheric communication between an inside and an outside of the outer tube through a filter member having air ventilation and waterproofing properties, the atmosphere communication hole extending in an axial direction thereof, wherein the gas sensor further includes: a protection portion that protects the filter member by covering the atmosphere communication hole of the seal member from the rear end of the gas sensor in the axial direction, the protection portion having a protrusion which protrudes toward a rear side of the gas sensor, and has an opening smaller than an opening of the atmosphere communication hole, wherein the protrusion is disposed at a further front end side of the rear end surface of the seal member.

As described above, in the gas sensor of the invention, a protrusion is disposed at a further front end side of the rear end surface of a seal member. In other words, since the protrusion is disposed in the seal member, a lead wire is not hooked by the edge of the protrusion when being installed. As a result, it is possible to prevent the lead wire from being damaged.

Also, since the protrusion is disposed in the seal member, flying stones do not easily collide with the protrusion, and thus the air ventilation of an opening formed in the protrusion may be favorably maintained. In addition, it is possible to prevent the filter member from being broken due to external impact caused by contact with plants or trees or collision with flying stones when a protection portion is deformed to expose the filter member.

Also, the protrusion may have a structure protruding from the protection portion toward the rear end side and having a smaller opening than the opening of the atmosphere communication hole. In detail, the protrusion may protrude with a dome shape or be formed by forming two grooves in the protection portion, and pressing a region between two grooves toward the rear end side.

In addition, the protection portion may have a greater hardness than the filter member. In this way, it is possible to more reliably prevent the filter member from being broken.

In a preferred embodiment (2), the gas sensor according to (1) above further comprises an arm extending from the protection portion in a radial direction, wherein the arm and the protection portion are integrally formed with an outer tube. If the arm, the protection portion, and the outer tube are integrally formed as mentioned above, the number of parts may be reduced.

In addition, in the gas sensor of the invention, the seal member may crimp the outer tube toward an inner side in the radial direction so that the seal member is held in the outer tube. Thus, in another preferred embodiment (3) of the gas sensor according to (2) above, the seal member is held in the outer tube by crimping the outer tube to an inner side thereof in the radial direction. Consequently, stress caused by the crimping is applied to the seal member so that the stopper expands toward the rear end of the gas sensor. Thus, the protrusion may be easily disposed at a further front end side of the rear end surface of the seal member by using a seal member that expands toward the rear end. As a result, it is possible to easily prevent the lead wire from being damaged.

In yet another preferred embodiment (4) of the gas sensor according to (1) above, the gas sensor includes a protection unit having an arm extending from the protection portion in a radial direction and a cylindrical portion connected to the arm and covering the periphery of the outer tube, wherein the cylindrical portion is mechanically fixed to the outer tube so that the protection unit is coupled to the outer tube. As mentioned above, the protection portion, the arm, and the cylindrical portion having a complex shape may be provided as a separate protection unit independently from the outer tube, and the arm and the protection portion may be easily coupled to the outer tube.

Also, in order to mechanically unite (fix) the cylindrical portion of the protection unit with the outer tube, the cylindrical portion may have an inner diameter smaller than the outer diameter of the outer tube so that the cylindrical portion is press-fit into the outer tube, or the cylindrical portion may have a plurality of slits along the axial direction so that the cylindrical portion is engaged with the outer tube by elastic deformation.

In yet another preferred embodiment (5) of the gas sensor according to (2) above, the seal member has a groove extending outwards in a radial direction at a rear end-facing surface of the seal member from the atmosphere communication hole while circumventing the lead wire insert hole, the groove having a cutout toward the front end of the seal member, wherein the arm is at least partially disposed in the groove of the seal member.

The groove provided in the seal member promotes drainage and prevents the deterioration of air ventilation by the atmosphere communication hole when the seal member is wet from the outside, whereas at least partially disposing the arm in the groove ensures that the arm does not collide with flying stones. In this way, it is possible to prevent the filter member from being exposed to the outside due to movement of the protection portion, caused by deformation of the arm. As a result, it is possible to prevent the filter member from being broken due to external impact such as contact with trees or plants or collision with flying stones.

In addition, since the arm is at least partially disposed in the groove of the seal member, it is possible to prevent the protection portion or the arm from rotating in a circumferential direction of the gas sensor, and it is also possible to prevent the lead wire from being damaged due to contact with the protection portion or the arm.

Also, in a case where the arm is disposed in a part of the groove, it is possible to prevent the protection portion or the arm from rotating in a circumferential direction of the gas sensor, or to prevent the arm from being deformed due to collision with flying stones. However, if the arm is disposed entirely in the groove, it is possible to more reliably prevent the protection portion or the arm from rotating in a circumferential direction of the gas sensor or to prevent the arm from being deformed due to a collision with flying stones.

In yet another preferred embodiment (6) of the gas sensor according to (5) above, a plurality of grooves extends outwards in the radial direction at the rear end surface of the seal member from the atmosphere communication hole while circumventing the lead wire insert hole, and a plurality of arms is disposed in the grooves of the seal member. Since a plurality of arms is provided, even though one arm is distorted, the distortion is lessened due to the other arms, and thus the protection portion may securely cover the atmosphere communication hole of the seal member from the outside of the outer tube. In addition, in a case where a plurality of arms is provided, circumferential rotation of the protection portion or the arm around the gas sensor may be reliably prevented since the arms are respectively disposed in the plurality of grooves. Also, it is possible to reliably prevent the lead wire from being damaged due to contact with the protection portion or the arm.

BRIEF DESCRIPTION OF THE DRAWINGS

Illustrative aspects of the invention will be described in detail with reference to the following figures wherein.

DETAILED DESCRIPTION OF THE PREFERRED EMBODIMENTS

Hereinafter, a gas sensor according to an embodiment of the invention is described with reference to the drawings. However, the present invention should not be construed as being limited thereto.

Figure 1:
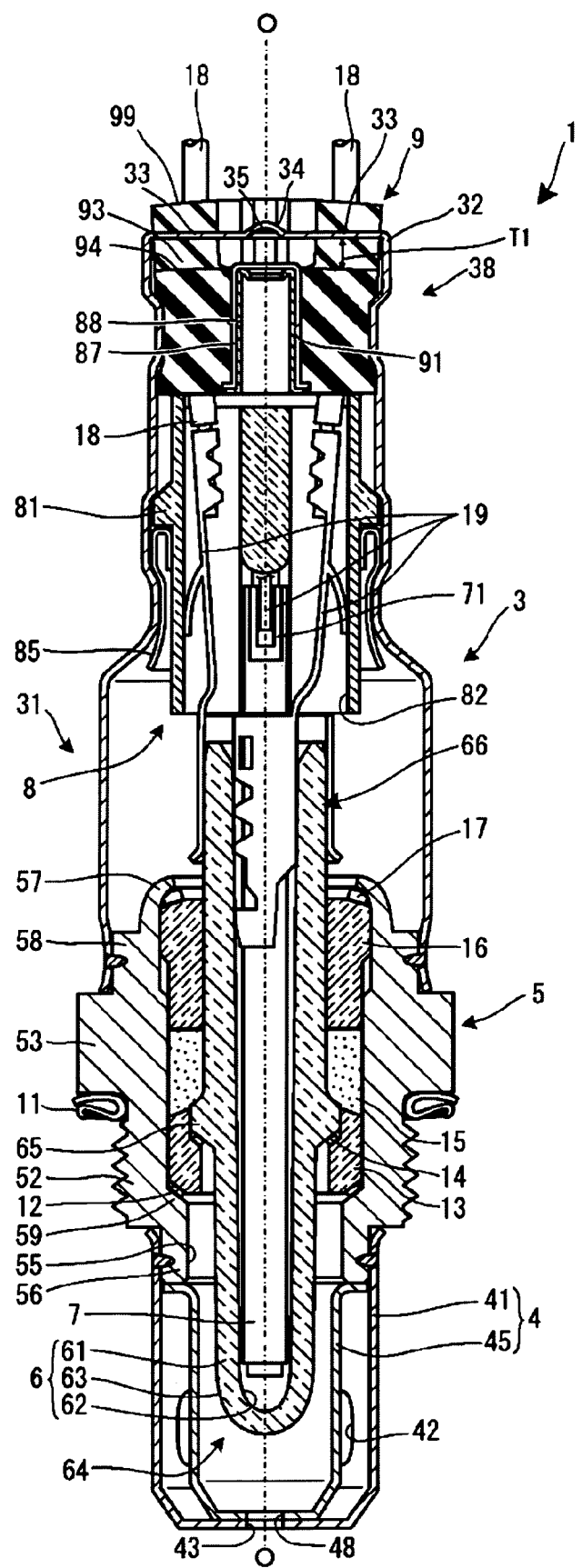
FIG. 1 is a vertical sectional view showing a structure of the gas sensor 1 according to a first embodiment.

First, as an example, a structure of a gas sensor 1 according to a first embodiment is described with reference to FIGS. 1 to 4. Also, the gas sensor 1 shown in FIG. 1 is mounted to an exhaust pipe (not shown) for discharging an exhaust gas exhausted from an engine of a vehicle or the like. Hereinafter, in an axial O direction of the gas sensor 1, a side directed to a front end side of a sensor element 6 inserted into the exhaust pipe (which is a closed side and a lower side in the figure) is taken as a front end side, and a side opposite thereto (which is an upper side in the figure) is taken as a rear end side.

The gas sensor 1 shown in FIG. 1 is a sensor for detecting the concentration of oxygen in an exhaust gas flowing in the exhaust pipe, and a cylindrical sensor element 6 having a thin and long cylindrical shape with a closed front end is held in a metal shell 5, an outer tube 3, or a protector 4. Lead wires 18 for extracting a signal output from the sensor element 6 or connecting electric current to a heater 7 mounted to the sensor element 6 are drawn from the gas sensor 1. Each lead wire 18 is electrically connected to a sensor controller (not shown) provided apart from the gas sensor 1 or an ECU (Electronic Control Unit) of a vehicle.

The sensor element 6 of the gas sensor 1 has a solid electrolyte body 61 containing zirconia, which is formed in a lower cylinder, and a reference electrode 62 made of Pt or a Pt alloy and having a porous shape is formed on an inner surface of the solid electrolyte body 61 so as to cover substantially the entire surface thereof. A front end side (or, a closed side) of the sensor element 6 is configured as a detection portion 64, and a detection electrode 63 provided at an outer surface thereof is exposed to the exhaust gas flowing in an exhaust pipe (not shown). Though not shown in the figure, the detection electrode 63 is coated with a porous electrode protection layer made of a heat-resisting ceramic and is protected from contamination by the exhaust gas. Also, a flange member 65 protruding outwards in a radial direction is provided at a substantially middle position of the sensor element 6 in an axial O direction. In addition, a rod-shaped heater 7 for heating and activating the solid electrolyte body 61 is inserted into the cylindrical hole of the sensor element 6.

The sensor element 6 is surrounded by a cylindrical metal shell 5 around its periphery in a radial direction, and the sensor element 6 is held in a cylindrical hole 55 of the metal shell 5. The metal shell 5 is a cylindrical member made of stainless steel such as SUS430, and a male screw 52 to be screwed with an attachment portion (not shown) of the exhaust pipe is formed at a front end side of the metal shell 5. A front end engagement portion 56 to be engaged with a protector 4, described below, is formed on an outer periphery of the metal shell 5 at a further front end side of the male screw 52. The detection portion 64 of the sensor element 6 protrudes at a further front end side of the front end engagement portion 56.

A tool engagement portion 53 having an enlarged diameter in a radial direction is formed at the rear end side of the male screw 52 of the metal shell 5, and a mounting tool used for mounting the gas sensor 1 to the attachment portion (not shown) of the exhaust pipe is engaged with the tool engagement portion 53. A ring-shaped gasket 11 for preventing gas leakage through the attachment portion of the exhaust pipe is inserted into a portion between the tool engagement portion 53 and the male screw 52. Also, a crimping portion 57 for crimping and fixing the sensor element 6 held in the cylindrical hole 55 of the metal shell 5 is provided at the rear side of the metal shell 5. The rear end portion 66 of the sensor element 6 protrudes at the further rear end side of the crimping portion 57. Also, a rear end engagement portion 58 to be engaged with the front end portion 31 of the outer tube 3, described below, is formed on an outer periphery between the tool engagement portion 53 and the crimping portion 57.

Next, a step portion 59 having an inner periphery protruding inwards in a radial direction is provided at the front end in the cylindrical hole 55 of the metal shell 5, and a cylindrical support member 13 made of alumina is locked at the step portion 59 by means of a metallic packing 12. The inner periphery of the support member 13 is also formed with a step, and the flange member 65 of the detector 6 is supported by the support member 13 by means of the metallic packing 14 disposed at the stepped portion. Also, a filling member 15 made of talc powder is filled in the cylindrical hole 55 at the rear end of the support member 13, and a cylindrical sleeve 16 made of alumina is disposed at the rear end of the filling member 15 so that the filling member 15 is positioned between the support member 13 and the sleeve 16.

An annular ring 17 is disposed at the rear end of the sleeve 16, and the sleeve 16 is pressed to the filling member 15 through the ring 17 since the crimping portion 57 of the metal shell 5 is crimped in a radial direction. By means of the additional crimping of the crimping portion 57, the filling member 15 is filled by pressure in the cylindrical hole 55 of the metal shell 5 so that the flange member 65 of the sensor element 6 is pressed toward the support member 13 locked by the step portion 59 of the metal shell 5, and a gap is air-tightly sealed between the inner peripheral surface of the cylindrical hole 55 and the outer peripheral surface of the sensor element 6. As mentioned above, the sensor element 6 is held in the cylindrical hole 55 of the metal shell 5 by means of each member sandwiched between the crimping portion 57 and the step portion 59 of the metal shell 5.

Then, the protector 4 covering the detection portion 64 of the sensor element 6 protruding from the front end engagement portion 56 toward the front end in the axial O direction may be assembled to the front end engagement portion 56 of the metal shell 5 by welding. The protector 4 protects the detection portion 64 of the sensor element 6 protruding in an exhaust pipe (not shown) when the gas sensor 1 is mounted to the exhaust pipe from water droplets or impurities included in the exhaust gas. The protector 4 has a double structure including an outer protector 41 constituting a lower cylinder and having a circumferential edge at an open side, which is fixed to the front end engagement portion 56, and an inner protector 45 of the lower cylinder, which is fixed to the outer protector 41. Introduction openings 42 for introducing the exhaust gas to the detection portion 64 of the sensor element 6 are respectively formed in the outer peripheral walls of the outer protector 41 and the inner protector 45 (where the gas introduction opening of the inner protector 45 is not shown). Also, discharge outlets 43, 48 for discharging water droplets or exhaust gas therein are respectively formed in lower walls of the outer protector 41 and the inner protector 45.

In addition, a cylindrical separator 8 made of an insulating ceramic is disposed at a further rear end side of the rear end portion 66 of the sensor element 6 in the axial O direction. The separator 8 has a receiving unit 82 that receives four connection terminals 19 (among which three connection terminals 19 are shown in FIG. 1) independently. The receiving unit 82 is pressed through the separator 8 in the axial O direction, and the separator 8 is constituted so that the front and rear ends of the separator 8 may be ventilated. The connection terminals 19 are respectively electrically connected to a reference electrode 62 of the sensor element 6, a detection electrode 63, and a pair of electrodes 71 (among which one electrode 71 is shown in FIG. 1) exposed to the rear end side for electric connection to a heating resistor of the heater 7. The separator 8 receives the connection terminals 19 in a separated state and prevents the connection terminals 19 from contacting each other. Core wires of four lead wires 18 (among which two lead wires 18 are shown in FIG. 18) are respectively crimped and fixed to the connection terminals 19, and each lead wire 18 is drawn out to the gas sensor 1 through a grommet 9, described below. Also, a flange member 81 protruding out in a radial direction is provided at the outer peripheral surface of the separator 8, and a substantially cylindrical holding bracket 85 is inserted into the outer peripheral surface at a further front end side of the flange member 81.

Figure 2:
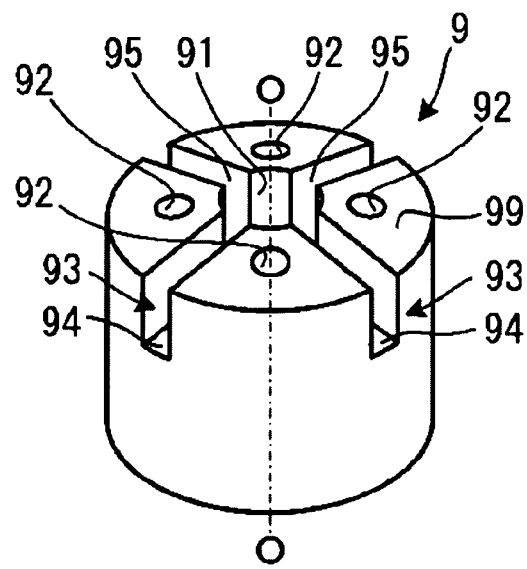
FIG. 2 is a perspective view showing a grommet 9 before being assembled.
Figure 3:
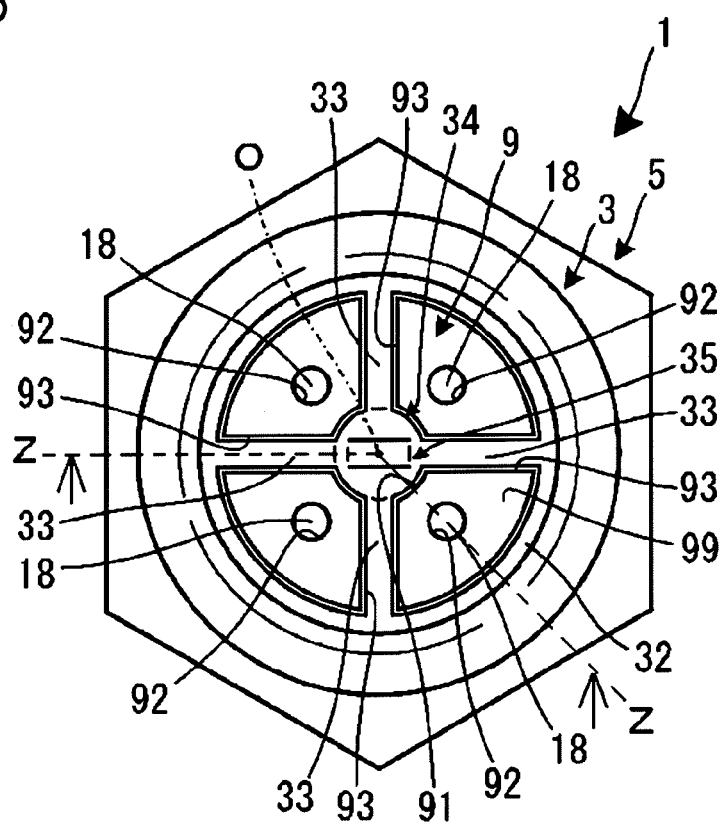
FIG. 3 shows the gas sensor 1, observed from a rear end in an axial O direction (from an upper side in FIG. 1)

In addition, the grommet 9 made of fluorine-based rubber is disposed at the rear end side of the separator 8. As shown in FIG. 2, the grommet 9 is a member formed in a substantially cylindrical shape with the axial O direction being in a height direction, and the grommet 9 has an atmosphere communication hole 91 and four lead wire insert holes 92, passing through in the axial O direction. The atmosphere communication hole 91 is formed at the center of the grommet 9 in a radial direction, and the lead wire insert holes 92 are respectively formed at regular intervals in a peripheral direction around the atmosphere communication hole 91 at a further outer end side of the atmosphere communication hole 91. The atmosphere communication hole 91 is further provided to introduce the atmosphere into the gas sensor 1 (or, into the outer tube 3, described below) through the receiving unit 82 of the separator 8, as shown in FIG. 1. In the outer tube 3, the sensor element 6 is fixed to the metal shell 5 while its rear end portion 66 is protruding, but the reference electrode 62 formed in the bottom-provided tube of the sensor element 6 may be exposed to the atmosphere. Also, as shown in FIG. 3, the four lead wires 18 are independently inserted into the four lead wire insert holes 92, respectively. Also, the grommet 9 corresponds to the "seal member" of the invention.

In addition, as shown in FIGS. 2 and 3, four grooves 93 extending with a groove shape along a radial direction toward the outer periphery from the location of the atmosphere communication hole 91 are formed in a rear end-facing surface 99 of the grommet 9, which is oriented toward a rear end side when the grommet 9 is assembled to the gas sensor 1. The groove 93 has a cutout toward the front end of the grommet 9 and has a bottom surface 94 and two side surfaces 95 connecting the bottom surface 94 with the rear end-facing surface 99. Each groove 93 is disposed between two adjacent lead wire insert holes 92 so as to circumvent the locations of four lead wire insert holes 92 opening on the rear end-facing surface 99. Thus, the rear end-facing surface 99 is divided into 4 sections by means of the grooves 93.

As shown in FIG. 1, a filter member 87 and its fastener bracket 88 are inserted into the atmosphere communication hole 91 of the grommet 9. The filter member 87 is for example a thin film-type filter having a micron-sized mesh structure made of a fluorine resin such as PTFE (polytetrafluoroethylene), and the filter member 87 allows passage of the atmosphere while not allowing the passage of water droplets. Also, the fastener bracket 88 is a cylindrical member and is fixed to the grommet 9 with the filter member 87 being interposed between the outer periphery of the fastener bracket 88 and the inner periphery of the atmosphere communication hole 91. The grooves 93 of the grommet 9 form channels so that water droplets, which can not pass through the filter member 87, flow toward the outer periphery and do not remain on the filter member 87. For this reason, the rear end of the filter member 87 may be disposed at the further rear end side of the bottom surface 94 of the groove 93. Also, the groove 93 may have an inclination oriented from the front end side to the rear side in the axial O direction as it approaches the central side from the outer side in a radial direction.

Figure 4:
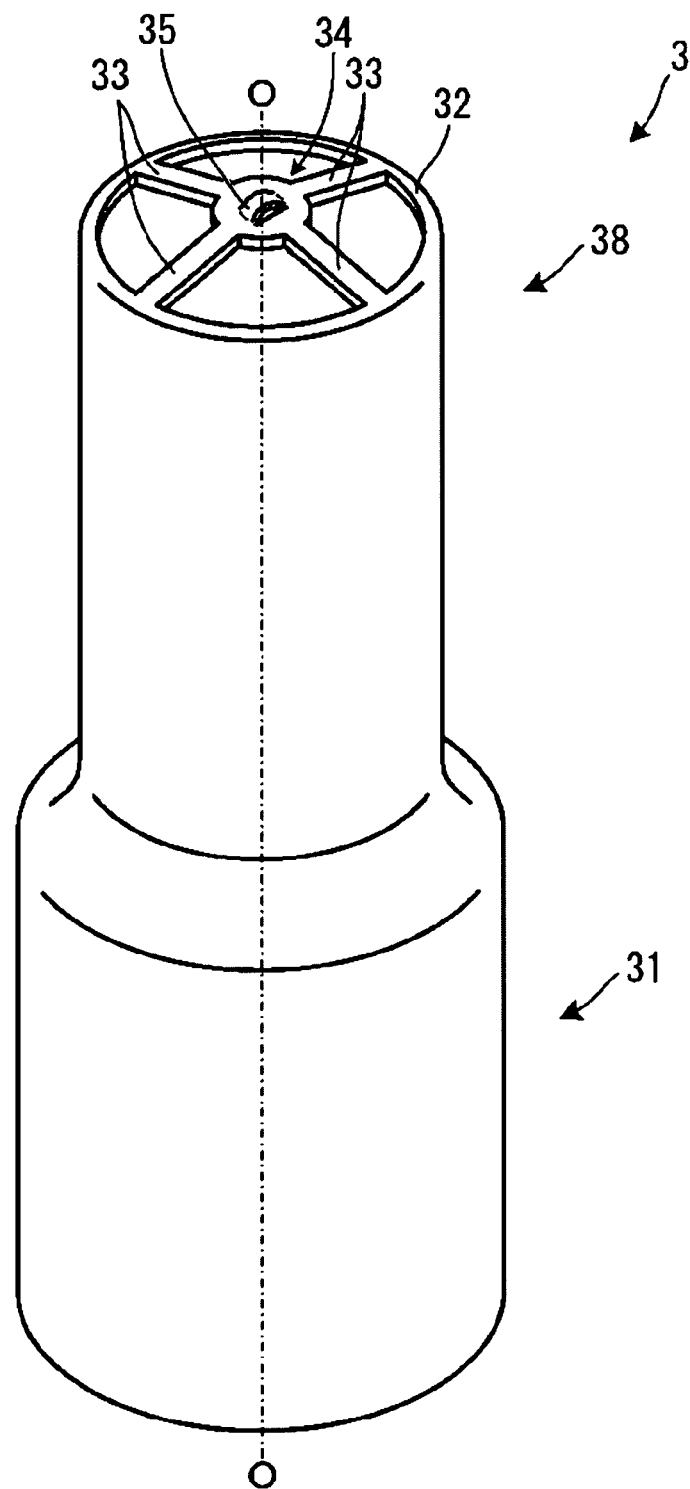
FIG. 4 is a perspective view showing an outer tube 3 before being assembled.

Then, the cylindrical outer tube 3 extending in the axial O direction may be assembled at the rear end side of the metal shell 5. As shown in FIG. 4, the outer tube 3 is made by processing stainless steel such as SUS304 into a cylindrical shape extending along the axial O direction, and then processing a front end portion 31 located at a front side (a lower side in FIG. 4) into a relatively greater diameter than the other portion of the outer tube 3. The inner diameter of the front end portion 31 is greater than the outer diameter of the rear end engagement portion 58 so that the front end portion 31 is engaged with the rear end engagement portion 58 (see FIG. 1) of the metal shell 5. Also, as shown in FIGS. 3 and 4, a rear end of the rear end portion 38 located at a rear end side of the outer tube 3 is bent inwards in a radial direction to form a connection portion 32, and four arms 33 having a plate shape extending in the axial O direction protrude from four locations in the circumferential direction of the connection portion 32.

In addition, each arm 33 is respectively connected to the outer periphery of a disk-shaped protection portion 34. The outer diameter of the protection portion 34 is substantially identical to that of the atmosphere communication hole 91 of the grommet 9, shown in FIG. 2, and the protection portion 34 is supported by the arm 33 as the protection portion 34 covers the atmosphere communication hole 91 so that its thickness direction is in agreement with the axial O direction, as shown in FIGS. 1 and 3. Also, as shown in FIG. 4, a protrusion 35 protruding toward the rear end of the protection portion 34 is formed. The opening provided in the protrusion 35 is smaller than the opening (size) of the atmosphere communication hole 91 (see FIG. 1), thereby preventing the ingression of flying stones or the like into the atmosphere communication hole 91. Also, the opening of the protrusion 35 ensures air ventilation between the outside and the atmosphere communication hole 91 (or, air ventilation between the inside and the outside of the outer tube 3). As the protection portion 34 is provided as described above, the filter member 87 disposed in the atmosphere communication hole 91 may be protected against external impact such as contact with plants or trees and collision with flying stones, and thus it is possible to prevent the filter member 87 from being broken.

The outer tube 3 configured as above is disposed at the rear end of the metal shell 5 while surrounding the side surfaces of the rear end portion 66 of the detector 6, the separator 8 and the grommet 9 aligned in the axial O direction, as shown in FIG. 1. The front end portion 31 of the outer tube 3 is fitted in the outer periphery of the rear end engagement portion 58 of the metal shell 5, and the outer tube 3 is crimped inwards in a radial direction from the outer periphery. Also, the outer tube 3 is fixed to the metal shell 5 by performing laser welding around the entire outer periphery of the front end portion 31.

In addition, the side surface of the outer tube 3 corresponding to a location at a further front end side of the flange unit 81 of the separator 8 is crimped inwards in a radial direction around the entire outer periphery thereof. The holding bracket 85 is disposed at this location, and the holding bracket 85 is crimped and held in the outer tube 3 while holding the separator 8 therein. Also, the side of the outer tube 3 corresponding to a location at a further rear end side of the flange unit 81 of the separator 8 is also crimped inwards in a radial direction at several locations in a peripheral direction. The additional crimping at the above region is performed at a location contacting the rear end of the flange member 81, and thus the flange member 81 is interposed between the crimped region and the holding bracket 85, thereby controlling the movement of the separator 8 in the axial O direction.

Also, if the outer tube 3 is fixed to the metal shell 5, as shown in FIG. 1, the protrusion 35 provided on the outer tube 3 is disposed at a further front end side of the rear end surface 99 of the grommet 9. In other words, the protrusion 35 is disposed in the grommet 9. In this way, the lead wire 18 is not hooked by the edge of the protrusion 35 when being installed. As a result, it is possible to prevent the lead wire 18 from being damaged.

In addition, since the protrusion 35 is disposed in the grommet 9, flying stones do not easily collide with the protrusion 35, and thus the opening formed in the protrusion 35 may favorably maintain air ventilation. In addition, it is possible to prevent the filter member 87 from being broken due to external impact such as contact with trees or plants or collision with flying stones when the protection portion 34 is deformed to expose the filter member 87.

Also, since the arm 33 and the protection portion 34 are formed integrally with the outer tube 3, the number of parts may be reduced.

In addition, as shown in FIG. 1, the rear end portion 38 of the outer tube 3 surrounding the outer periphery of the grommet 9 is crimped inwards in the radial direction from the outer periphery, and the grommet 9 is fixed to the outer tube 3. Since the outer tube 3 is crimped inwards in the radial direction as mentioned above, in a configuration where the grommet 9 is held in the outer tube 3, the grommet 9 expands at the rear end of the gas sensor 1 since the stress caused by the crimping is applied to the grommet 9. Thus, the protrusion 35 may be more easily disposed at a further front end side of the rear end surface 99 of the grommet 9 by using the expansion of the grommet 9 at the rear end. As a result, it is possible to easily prevent the lead wire 18 from being damaged.

Also, as shown in FIG. 1, while the arms 33 are disposed in the rear end portion 38 of the outer tube 3 and the grommet 9 disposed at the rear side of the separator 8, the rear end surface 99 of the grommet 9 divided into four sections protrudes toward the rear end from the outer tube 3 except for the regions between the four arms 33, and the arms 33 are disposed in the grooves 93 as shown in FIG. 3. Since the arms 33 are disposed in the grooves 93, flying stones do not easily collide with the arms 33. In this way, it is possible to prevent the filter member 87 from being exposed to the outside due to the movement of the protection portion 34, caused by deformation of the arm 33. As a result, it is possible to prevent the filter member 87 from being broken due to external impact such as contact with trees or plants or collision with flying stones.

In addition, since the arm 33 may be disposed in the groove 93 of the grommet 9, it is possible to prevent the protection portion 34 or the arm 33 from rotating in a circumferential direction of the gas sensor 1, and it is also possible to prevent the lead wire 18 from being damaged due to contact with the protection portion 34 or the arm 33.

Also, as shown in FIG. 1, the arm 33 is disposed while forming a gap T1 with the bottom surface 94 of the groove 93. In this way, even though the grommet 9 thermally expands due to the heat received from the exhaust pipe or the exhaust gas or expands at the rear side of the gas sensor 1, the groove 93 of the grommet 9 is not hooked by the arm 33. As a result, the groove 93 of the grommet 9 does not expand with a different ratio from other regions (for example, the four regions that constitute the rear end surface 99), and it is possible to suppress the generation of cracks in the groove 93 of the grommet 9.

Also, since a plurality of arms 33 is used, even though one arm 33 is distorted, the other arms 33 lessen the distortion, and thus the protection portion 34 may securely cover the atmosphere communication hole 91 of the grommet 9 from the rear side of the outer tube 3. In addition, in the case where a plurality of arms 33 is used, since the arms 33 are respectively disposed in the plurality of grooves 93 provided in the grommet 9, it is possible to reliably prevent the protection portion 34 or the arms 33 from rotating in a circumferential direction of the gas sensor 1, and it is also possible to prevent the lead wire 18 from being damaged due to contact with the protection portion 34 or the arm 33.

Next, one example of a method for producing the gas sensor 1 is described in the following sequence.

Figure 5:
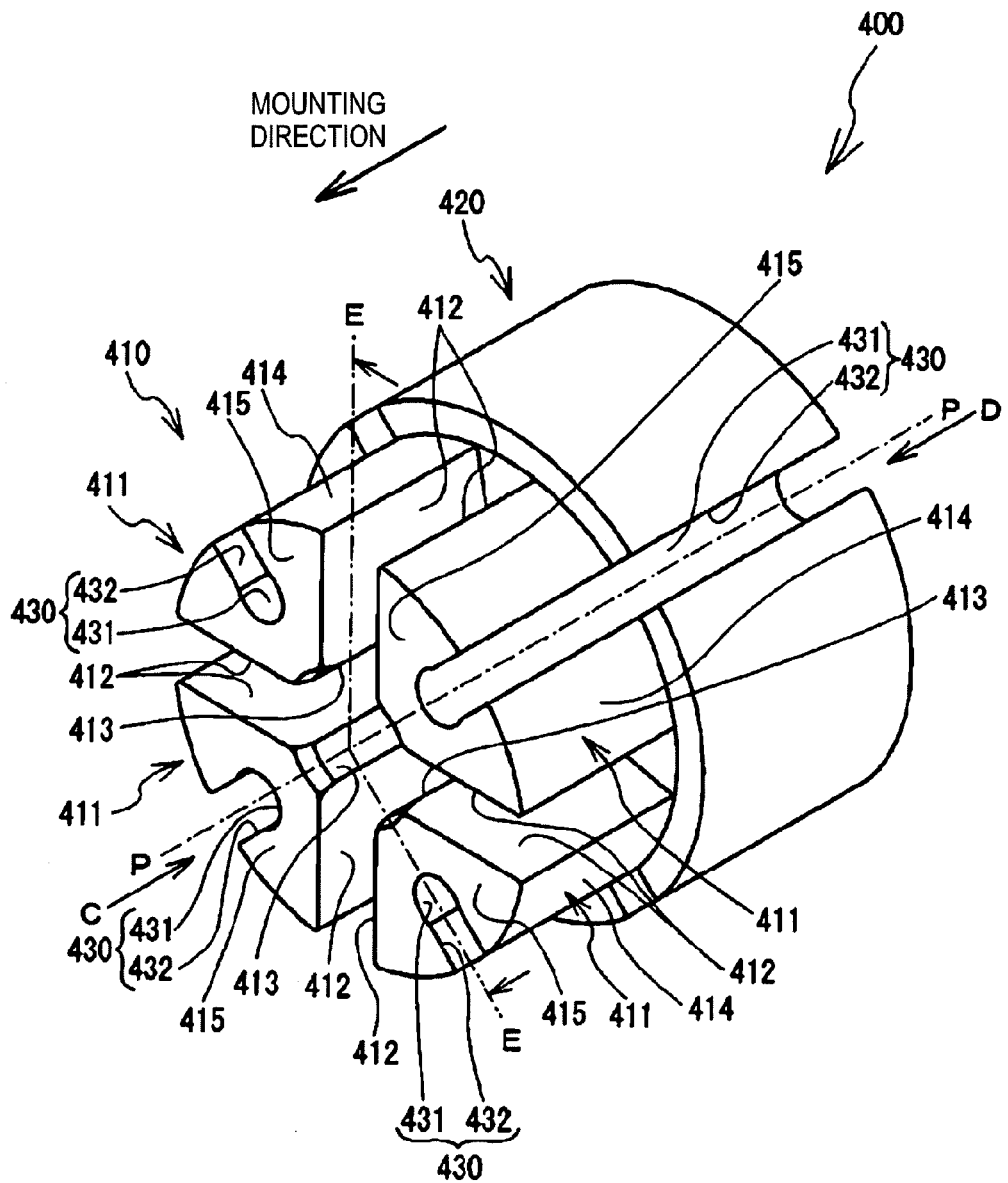
FIG. 5 is a perspective view showing a mounting jig 400.
Figure 6:
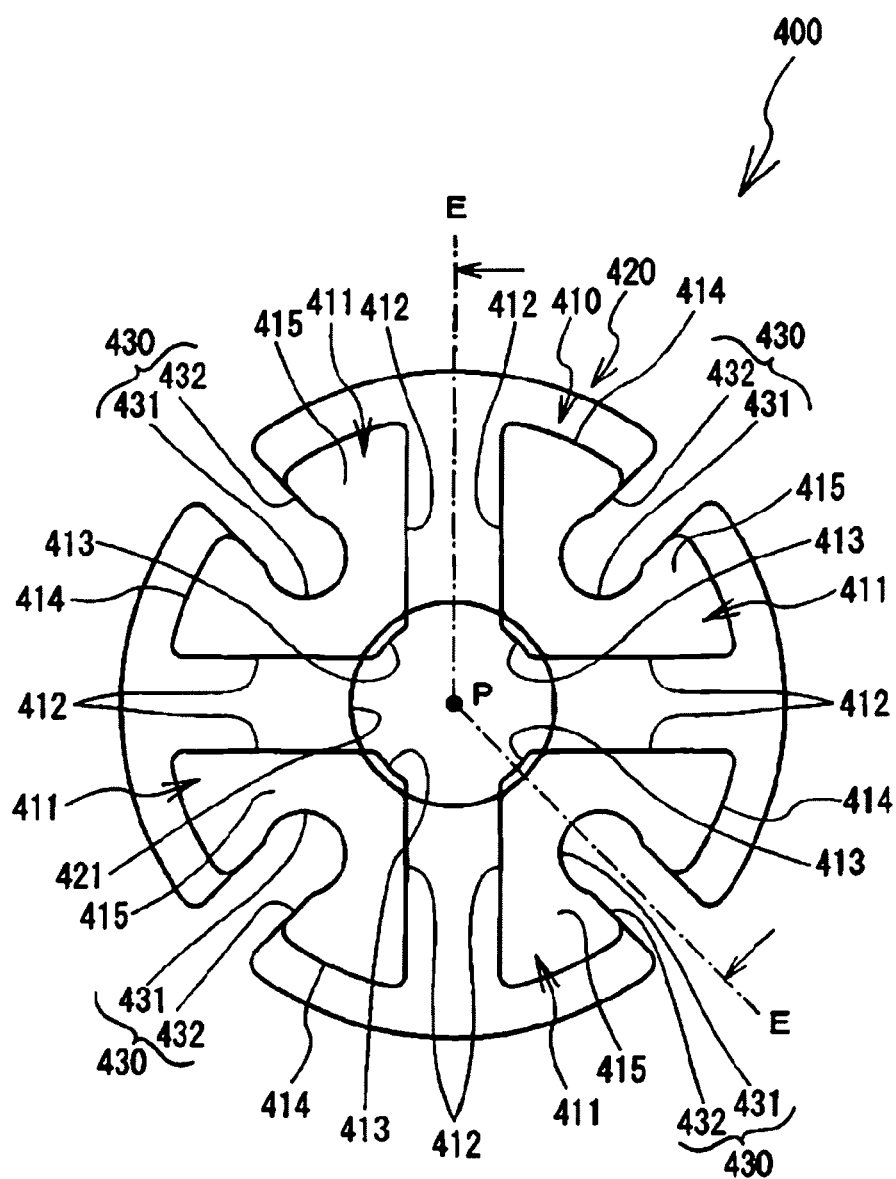
FIG. 6 shows the mounting jig 400, observed from a front side in a mounting direction (in an arrow C direction in FIG. 5)
Figure 7:
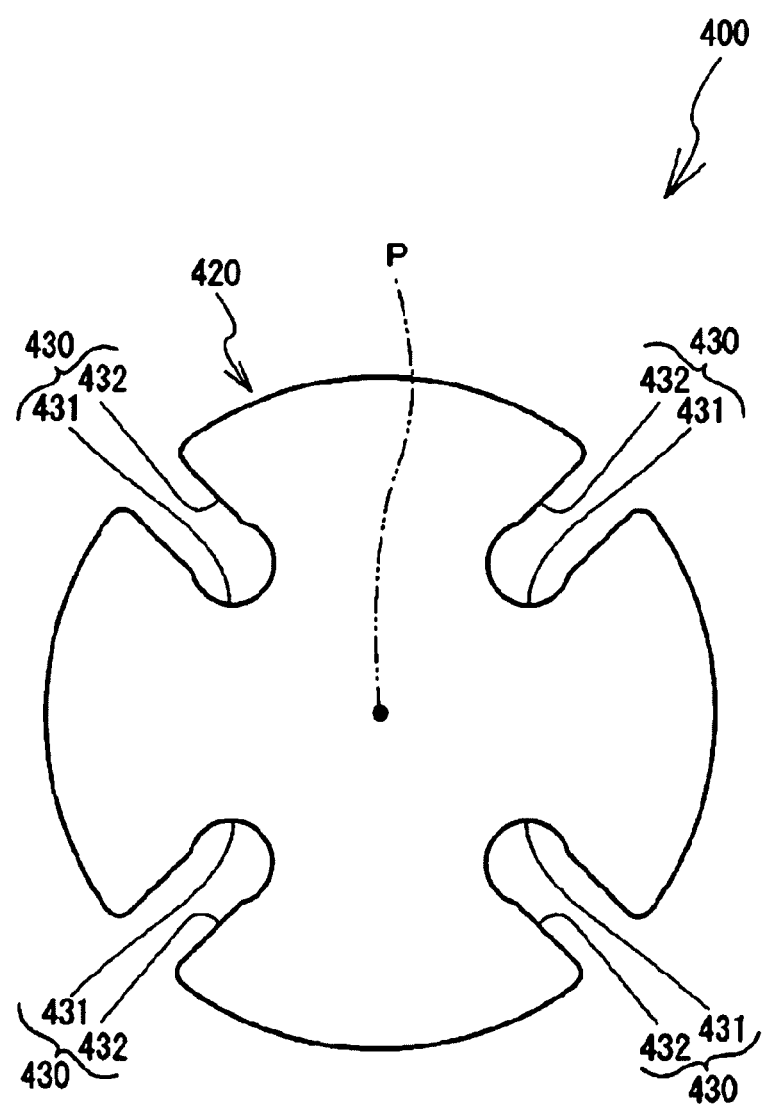
FIG. 7 shows the mounting jig 400, observed from a rear side in the mounting direction (in an arrow D direction in FIG. 5)
Figure 8:
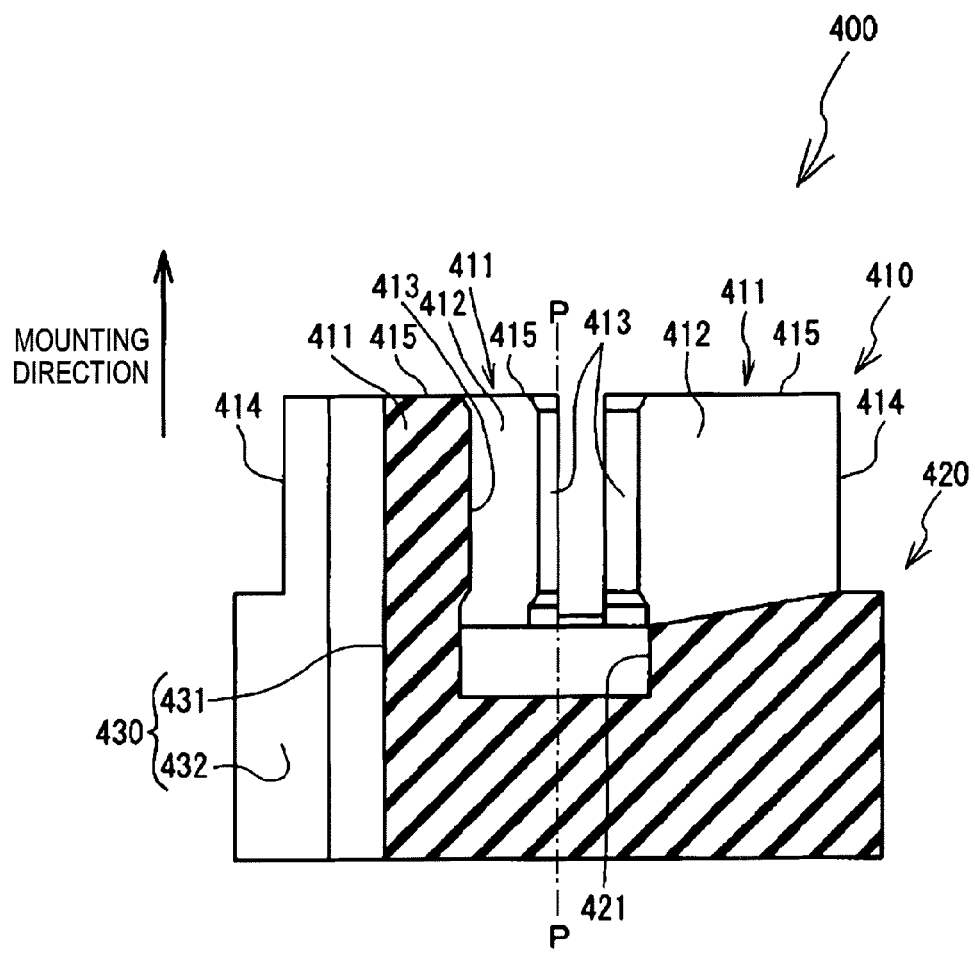
FIG. 8 is a bent sectional view showing the mounting jig 400, observed in an arrow direction of the bent line E-E represented by a two-dot chain line in FIG. 5 (or FIG. 6)

First, the structure of a mounting jig 400 used for producing the gas sensor 1 will be described with reference to FIGS. 5 to 8. FIG. 5 is a perspective view showing the mounting jig 400. FIG. 6 shows the mounting jig 400, observed from a front side in the mounting direction (in an arrow C direction in FIG. 5). FIG. 7 shows the mounting jig 400, observed from a rear side in the mounting direction (in an arrow D direction in FIG. 5). FIG. 8 is a sectional view showing a bend of the mounting jig 400, observed in an arrow direction of the bent line E-E represented by a two-dot chain line in FIG. 5 (or FIG. 6).

The mounting jig 400 shown in FIG. 5 is a jig for disposing the outer tube 3 when assembling the gas sensor 1 (see FIG. 1), and for example, the mounting jig 400 is made of NBR (nitrile rubber) and has a cylindrical shape with a central axis P (represented by a one-dot chain line in the figure) in the mounting direction. As shown in FIGS. 5 to 8, the mounting jig 400 has a base 420 in which diameter is enlarged in the rear side of the mounting direction and has a stepped shape, and a holding unit 410 is formed so as to protrude from the base 420 toward the front side in the mounting direction. The holding unit 410 is used for holding the outer tube 3 integrally with the mounting jig 400, and in detail, four protrusions 411 capable of being inserted into the gap (see FIG. 4) surrounded by the protection portion 34, the arm 33, and the rear end portion 38 of the outer tube 3 are arranged in a row in a circumferential direction. When the outer tube 3 is held, the arm 33 is inserted between sides 412 of adjacent two protrusions 411 in the circumferential direction of the central axis P.

Also, the inner side 413 toward the central axis P of each protrusion 411 surrounds the central axis P to form a passage into which the protection portion 34 is inserted. At this time, the passage has an inner diameter slightly smaller than the outer diameter of the protection portion 34 so that a load is applied to the protection portion 34. Also, as shown in FIG. 8, the passage formed by the inner side 413 is enlarged near a root of the base 420 of the holding unit 410, and, if the protection portion 34 moves to that position, the protection portion 34 is released from the load applied from each inner side 413. At this time, in order to prevent contact between the protection portion 34 and the base 420, a concave receiving unit 421 in communication with the passage formed by the inner side 413 of the protrusion 411 is formed in the base 420. Also, the outer side 414 of the protrusion 411 is arranged at a location forming a gap with the rear end portion 38 of the outer tube 3. However, even though the protrusion 411 of the holding unit 410 respectively protrudes from the base 420, the protruding length of the protrusion 411 from the base 420 is adjusted so that the outer tube 3 does not come into contact with the bottom surface 94 of the groove 93 of the grommet 9.

This is at a time when the front end surface 415 of the outer tube holding unit 410 in the mounting direction contacts the rear end-facing surface 99 of the grommet 9, during the producing process of the gas sensor 1, described below. In other words, when the outer tube 3 is held in the mounting jig 400, the front end surface 415 of the protrusion 411 is disposed at least at a further front end side of the arm 33 in the mounting direction.

In addition, as shown in FIGS. 5 to 8, four lead wire holding units 430 having a groove shape through the rear end surface of the base 420 in the mounting direction from the front end surface of the holding unit 410 in the mounting direction along the central axis P are formed in the outer peripheral surface of the mounting jig 400. The lead wire holding unit 430 includes a bottom wall 431 having a circular cross-section and provided at a center location in the section of each protrusion 411 with respect to the central axis P of the holding unit 410, and side walls 432 facing each other with a width narrower than the inner diameter of the bottom wall 431 (the diameter of its cross-section). The inner diameter of the bottom wall 431 is substantially identical to the outer diameter of the lead wire 18 (see FIG. 1) of the gas sensor 1. Even though the lead wire 18 is disposed in the bottom wall 431 when the lead wire 18 is inserted into the lead wire holding unit 430, the side walls 432 prevent the lead wire 18 from being separated since the side wall 432 has a width narrower than the outer diameter of the lead wire 18. In addition, the arrangement of the central axes P of the four bottom walls 431 with respect to the cross-section orthogonal to the central axes P is substantially identical to the arrangement of the axes O of the four lead wire insert holes 92 with respect to the cross-section orthogonal to the axes O of the grommet 9. In this way, the lead wire insert hole 92 of the grommet 9 is connected to the bottom wall 431 of the mounting jig 400 when the front end surface 415 of the outer tube holding unit 410 in the mounting direction comes in contact with the rear end-facing surface 99 of the grommet 9. Also, the outer diameter of the base 420 is formed to be deeper than the outer diameter of the outer surface 414 of the protrusion 411. For this reason, the depth of the groove of the lead wire holding unit 430 in the base 420 is greater than the depth of the groove in the holding unit 410, and the side wall 432 more securely prevents separation of the lead wire 13 from the base 420.

Figure 9:
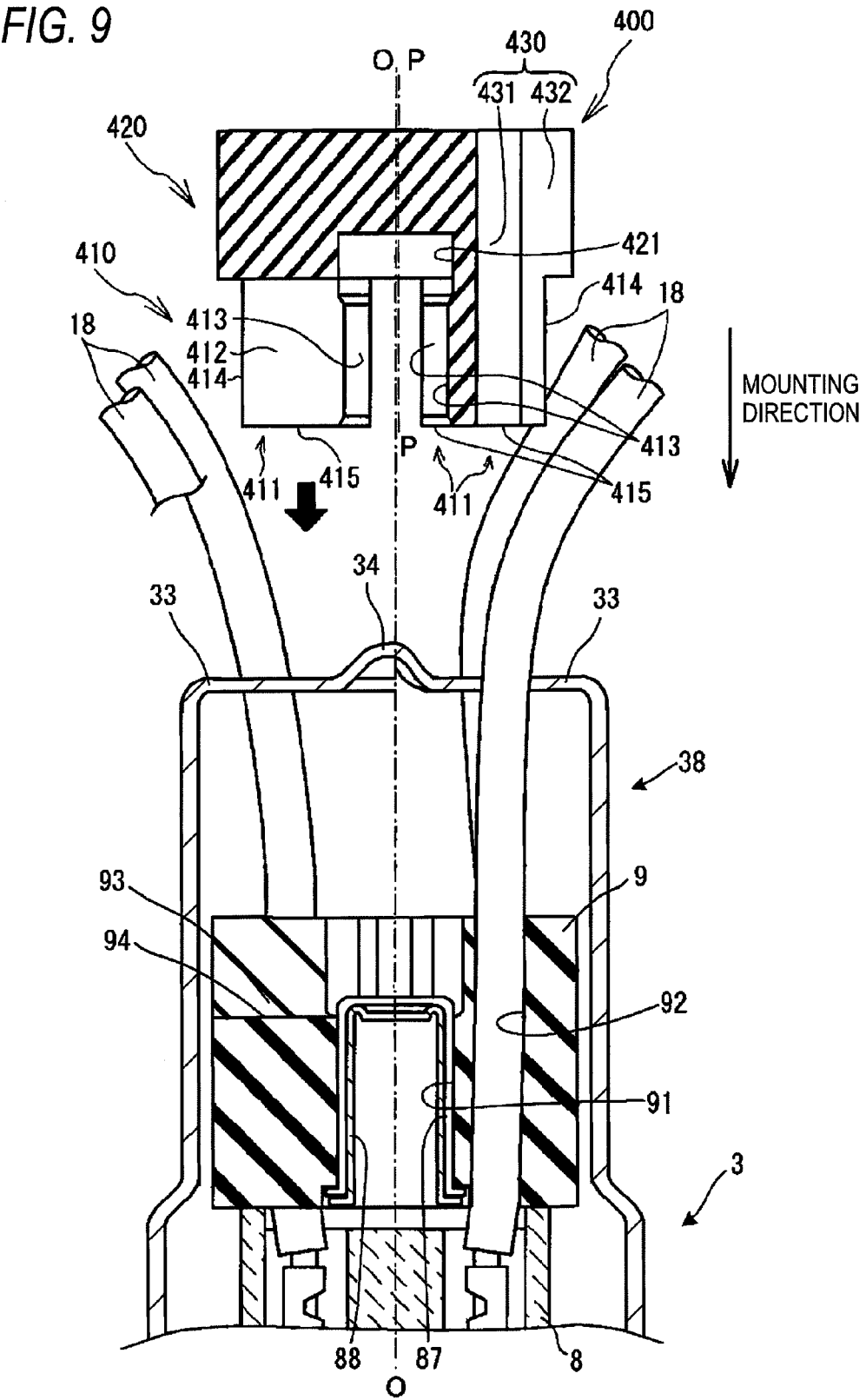
FIG. 9 illustrates a holding process.
Figure 10:
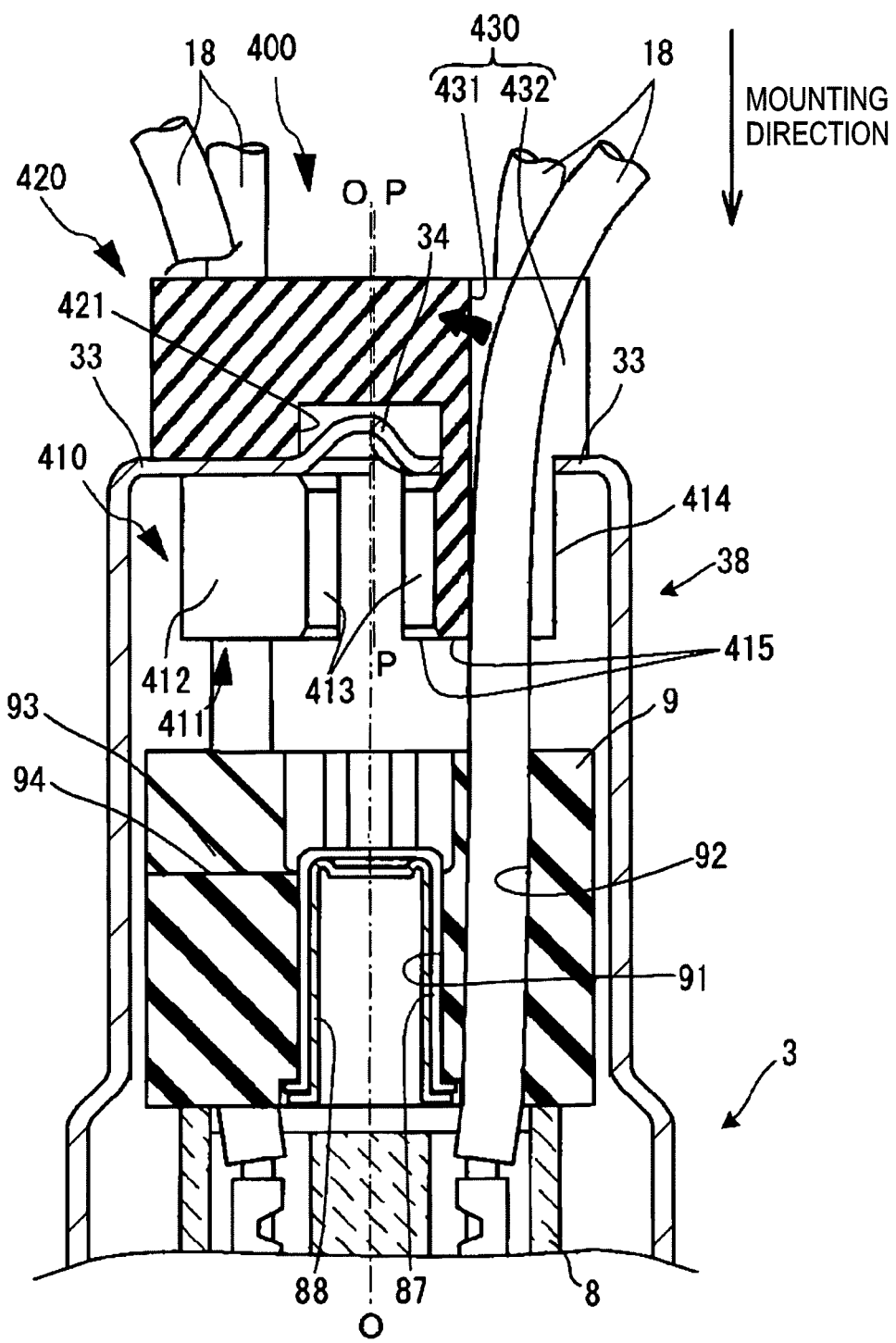
FIG. 10 illustrates a lead wire holding process.
Figure 11:
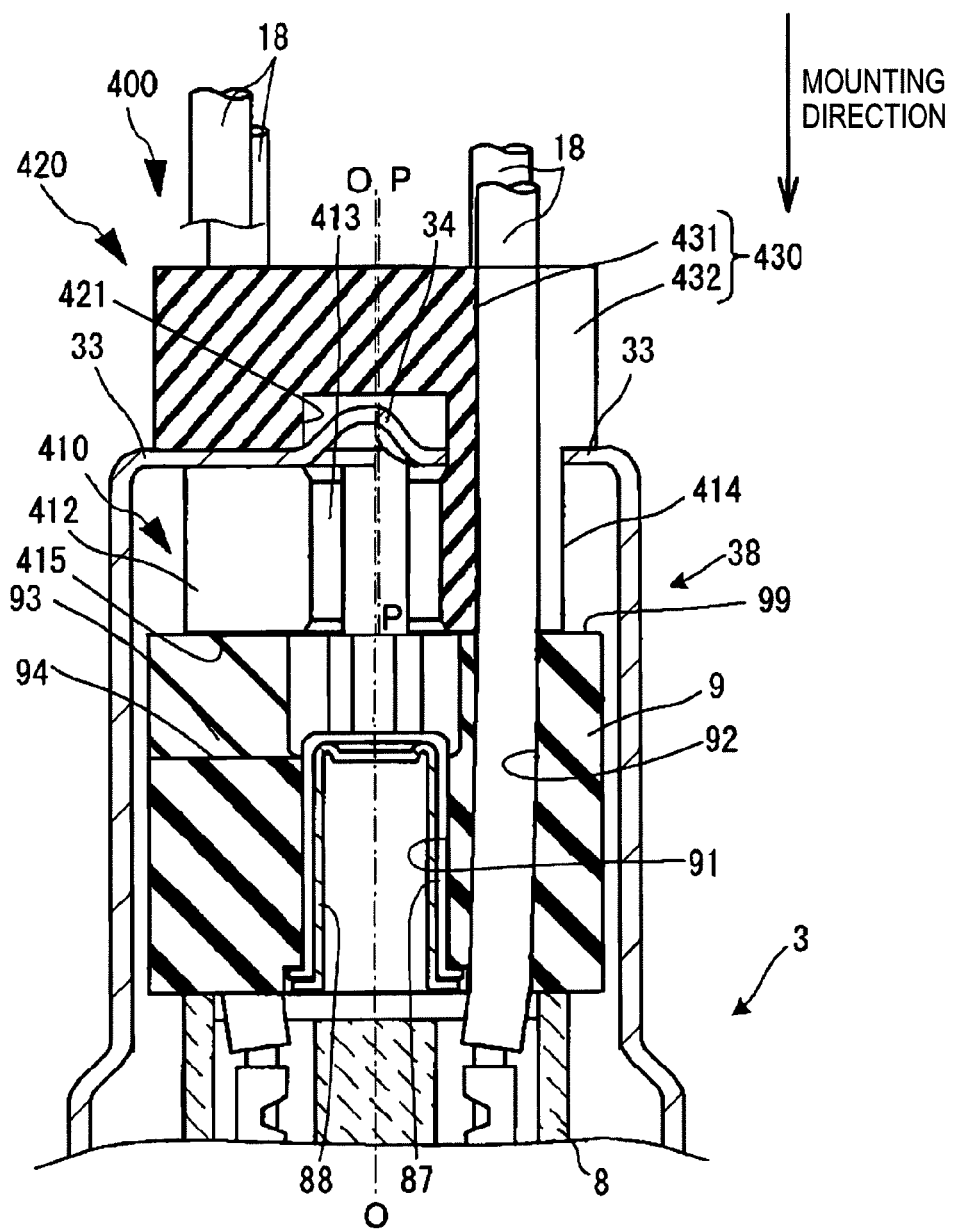
FIG. 11 illustrates a disposing process.
Figure 12:
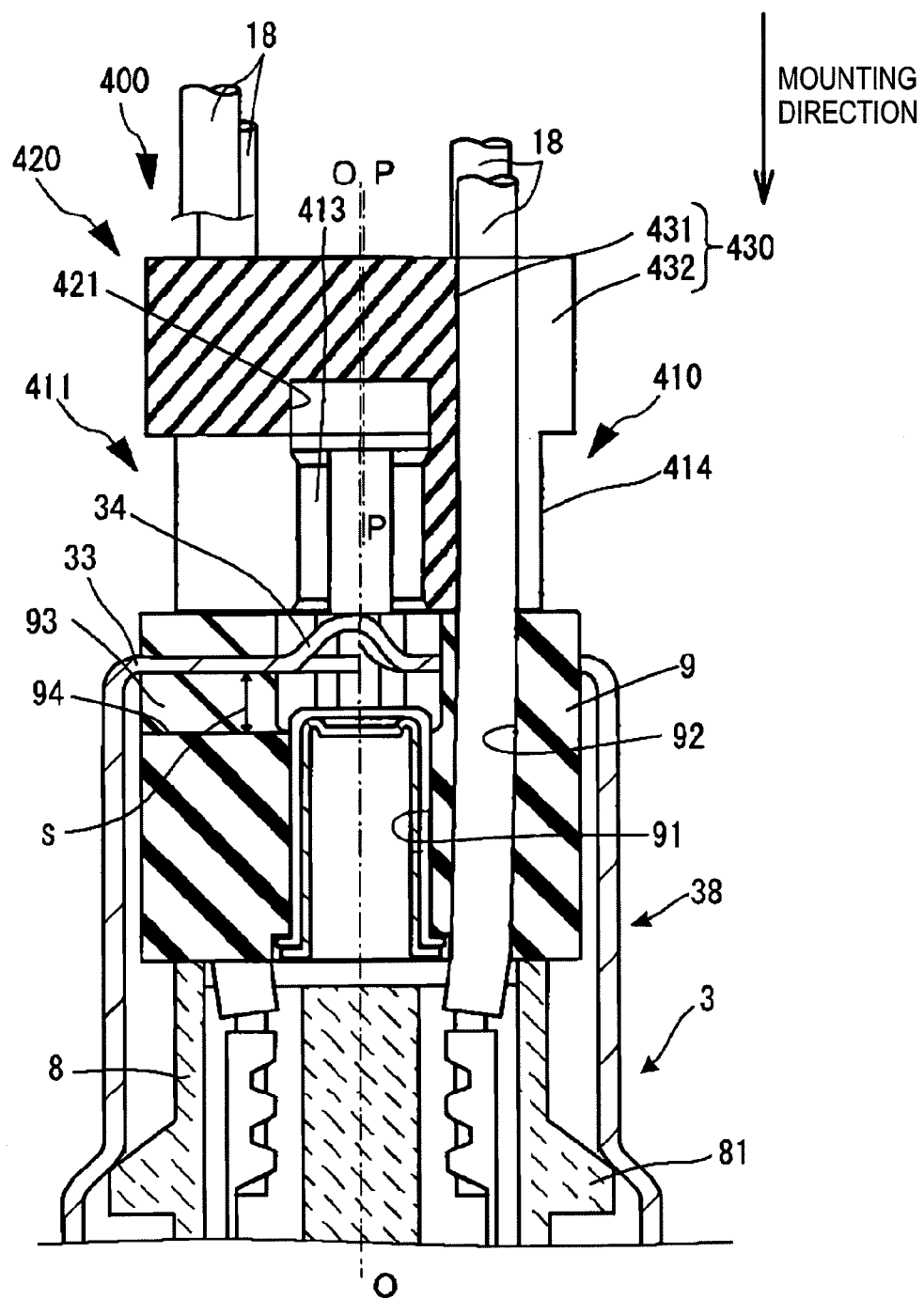
FIG. 12 illustrates a shifting process.

Next, the method for producing the gas sensor 1 using the mounting jig 400 will be described with reference to FIGS. 9 to 12. FIG. 9 illustrates the holding process. FIG. 10 illustrates the lead wire holding process. FIG. 11 illustrates the arranging process. FIG. 12 illustrates the shifting process. Also, the sectional views of the gas sensor 1 or the mounting jig 400 in FIGS. 9 to 12 are based on the case of being viewed in an arrow direction in the bent line Z represented by a dotted line in FIG. 3. Hereinafter, the process of mounting the outer tube 3 to the grommet 9 is described, but the other producing processes in relation to the gas sensor 1 are already well-known and thus will not be described in detail here.

The metal shell 5 of the gas sensor 1 shown in FIG. 1 is produced by forging a rod-shaped steel made of stainless steel such as SUS430, then cutting the steel to form a tool engagement portion 53 or a rear end engagement portion 58, a male screw 52, a cylindrical hole 55, and the like, and then performing rolling to form a thread at the male screw 52. Also, the sensor element 6 is produced by forming a reference electrode 62 or a detection electrode 63 by means of, for example, plating on the surface of a solid electrolyte body 61 formed in a lower cylinder, then forming an electrode protection layer by covering the surface of the detection electrode 63, and then firing the electrode protection layer. In addition, a protector 4 produced separately is adhered to the metal shell 5 by welding, and the sensor element 6 is crimped and held in the cylindrical hole 55 of the metal shell 5, thereby producing an intermediary body of the front end of the gas sensor 1.

Meanwhile, core wires of lead wires 18 of four connection terminals 19 made of conductive plates are adhered by additional crimping, among which two connection terminals 19 are connected to the electrode 71 of the heater 7. Along with receiving the connection terminals 19 and the heater 7 in the separator 8, the lead wires 18 are inserted into the separator 8 and the grommet 9. Also, the filter member 87 and the fastener bracket 88 are inserted into the atmosphere communication hole 91 of the grommet 9.

[Holding Process]

Then, as shown in FIG. 9, the four lead wires 18 drawn from the lead wire insert hole 92 of the grommet 9 are respectively inserted into gaps (see FIG. 4) surrounded by the protection portion 34, the arms 33, and the rear end portion 38 of the outer tube 3 so that the lead wires 18 do not contact the arms 33 or the protection portion 34. In this state, the front side of the mounting jig 400 in the mounting direction is arranged toward the outer tube 3 so that the central axis P is arranged in agreement with the axis O of the outer tube 3. Also, each protrusion 411 of the holding unit 410 is inserted into each gap surrounded by the protection portion 34, the arm 33, and the rear end portion 38 of the outer tube 3. In other words, the arm 33 is placed between the sides 412 of adjacent protrusions 411 in the circumferential direction with respect to the central axis P, and the protection portion 34 is respectively disposed between the inner sides 413 of four protrusions 411, which face the central axis P. In this connection, the mounting jig 400 and the outer tube 3 are positioned with respect to each other. Also, if the mounting jig 400 is moved in the mounting direction along the axis O as is and the protection unit 34 of the outer tube 3 is received in the receiving unit 421 of the mounting jig 400, the inner side 413 prevents the protection portion 34 from being separated (see FIG. 10), and the outer tube 3 is held integrally with the mounting jig 400.

[Lead Wire Holding Process]

Then, as shown in FIG. 10, four lead wires 18 are respectively inserted into a gap between adjacent side walls 432 of the lead wire holding unit 430 provided to the protrusions 411 of the mounting jig 400, and disposed to be held in a bottom wall 431. The lead wire 18 prevents each side wall 432 having a smaller width than the outer diameter thereof from being separated, and each lead wire 18 is disposed to be held in the bottom wall 431. Thus, the lead wire 18 is surrounded by the protrusion 411 and protected against contact with the protection portion 34, the arm 33, and the rear end portion 38 of the outer tube 3.

[Disposing Process]

As described above, the mounting jig 400 is made of NBR, and thus the mounting jig 400 allows the lead wire 18 to slide thereon while holding the lead wire 18 in the bottom wall 431 of the lead wire holding unit 430. As shown in FIG. 11, if the outer tube 3 integrally held to the mounting jig 400 is slid in an extension direction of the lead wire 18, the mounting jig 400 and the outer tube 3 are guided by the lead wire 18 and reach the rear end side of the grommet 9. Since the outer tube 3 and the lead wire 18 are positioned with respect to each other so that the lead wire 18 does not contact the outer tube 3 due to the mounting jig 400, the outer tube 3 does not graze or damage the lead wire 18 while sliding.

When the mounting jig 400 and the outer tube 3 reach the rear end side of the grommet 9, the front end surface 415 of the mounting jig 400 comes into contact with the rear end-facing surface 99 of the grommet 9 due to the protruded length of the protrusion 411 from the base 420 before the arm 33 of the outer tube 3 contacts the bottom 94 of the groove 93 of the grommet 9. At this time, the bottom wall 431 of the lead wire holding unit 430 of the mounting jig 400 is disposed in connection with the lead wire insert hole 92 of the grommet 9 by the guidance of the lead wire 18. Since the mounting jig 400 is positioned with respect to the grommet 9 in this way, the region between the sides 412 of the protrusions 411 is connected to each groove 93 of the grommet 9, and the passage formed in the inner side 413 is connected to the atmosphere communication hole 91 of the grommet 9.

[Shifting Process]

Also, as shown in FIG. 12, the outer tube 3 is pressed in the mounting direction along the axis O. The protection portion 34 of the outer tube 3 is guided toward the atmosphere communication hole 91 of the grommet 9 by the inner side 413 of the protrusion 411 of the mounting jig 400, and the arm 33 is guided between the sides 412 of the protrusions 411 toward each groove 93 of the grommet 9. In addition, the arm 33 is received in each groove 93 of the grommet 9, and the protection portion 34 is disposed in a region extending from the inner periphery of the atmosphere communication hole 91 in the axial O direction at the rear end of the filter member 87 to block the atmosphere communication hole 91. At this time, the flange member 81 of the separator 8 is engaged with the outer tube 3 so that the arm 33 does not come into contact with the bottom surface 94 of the groove 93, but the arm 33 is disposed with the gap S from the bottom surface 94 of the groove 93. Also, the gap S has a length greater than the gap T1. Since the grommet 9 is fixed by the outer tube 3 due to the additional crimping in a subsequent process, the above dimension is set while considering the fact that the grommet 9 expands to the rear end.

Since the mounting jig 400 contacts the grommet 9 before the outer tube 3 contacts the bottom surface 94 of the groove 93 as described above, a passage for guiding the arm 33 or the protection portion 34 to the groove 93 or the atmosphere communication hole 91 respectively is formed, and then the outer tube 3 is engaged with the grommet 9. At this time, as the protection portion 34 is separated from the filter member 87, the arm 33 is pressed so that the arm 33 of the outer tube 3 is disposed in the groove 93 of the grommet 9. In this way, as shown in FIG. 12, when the filter member 87 is assembled to the grommet 9, even though the filter member 87 is exposed at a further rear end side of the groove 93, it is possible to prevent the protection portion 34 of the outer tube 3 from contacting the grommet 9 and to also prevent the filter member 87 from being broken when grommet 9 is fitted into the outer tube 3.

In addition, since the separator 8 and the grommet 9 are not assembled to the outer tube 3 while the arm 33 presses the bottom surface 94 of the groove 93, it is possible to prevent the generation of cracks in the groove 93 of the grommet 9, which occurs when the groove 93 of the grommet 9 shrinks due to the arm 33. Furthermore, the ratio of shrinkage at the groove 93 of the grommet 9 is different from other regions of the grommet 9 (for example, the four regions that constitute the rear end-facing surface 99).

In the following process, the mounting jig 400 is removed, and the holding bracket 85 is inserted between the outer tube 3 and the separator 8 to crimp the outer tube 3 so that the separator 8 is held to the outer tube 3. Also, the rear end portion 38 of the outer tube 3 is crimped to fix the grommet 9 to the outer tube 3, also the front end portion 31 of the outer tube 3 is engaged with the rear end engagement portion 58 of the metal shell 5, and the region around the front end portion 31 is crimped and laser-welded, thereby producing the gas sensor 1.

Figure 13:
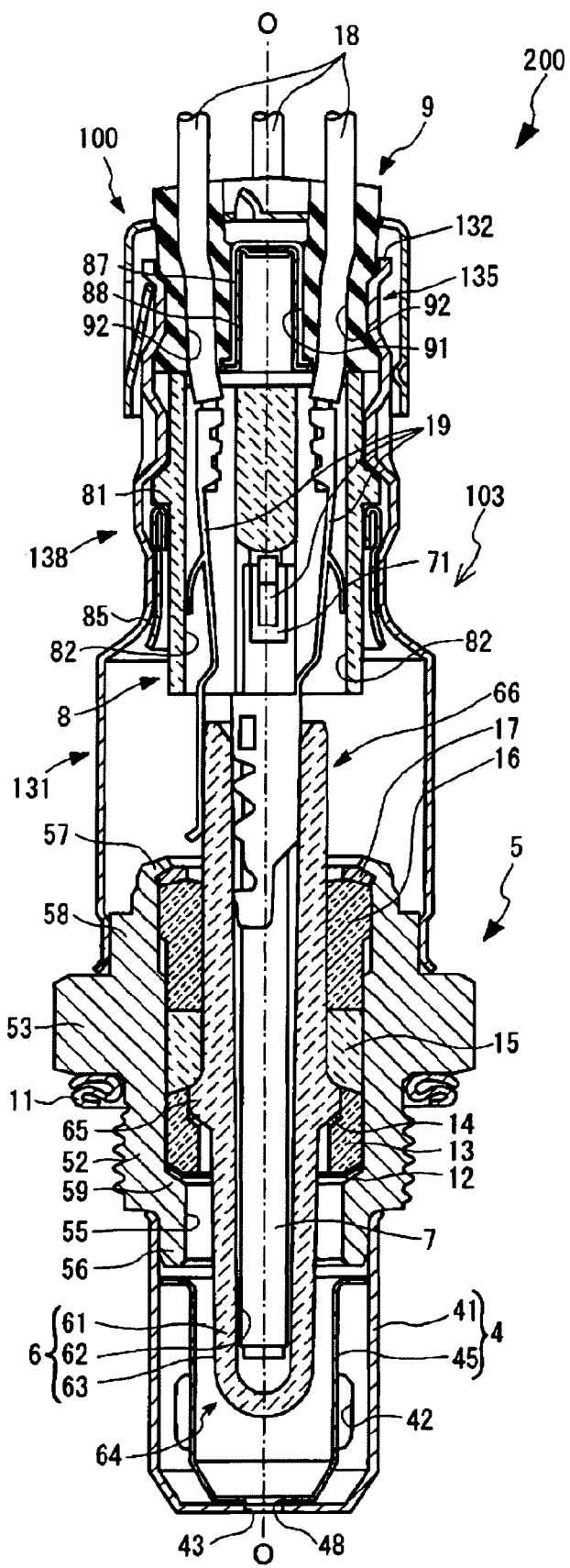
FIG. 13 is a vertical sectional view showing a structure of the gas sensor 200 according to a second embodiment.
Figure 14:
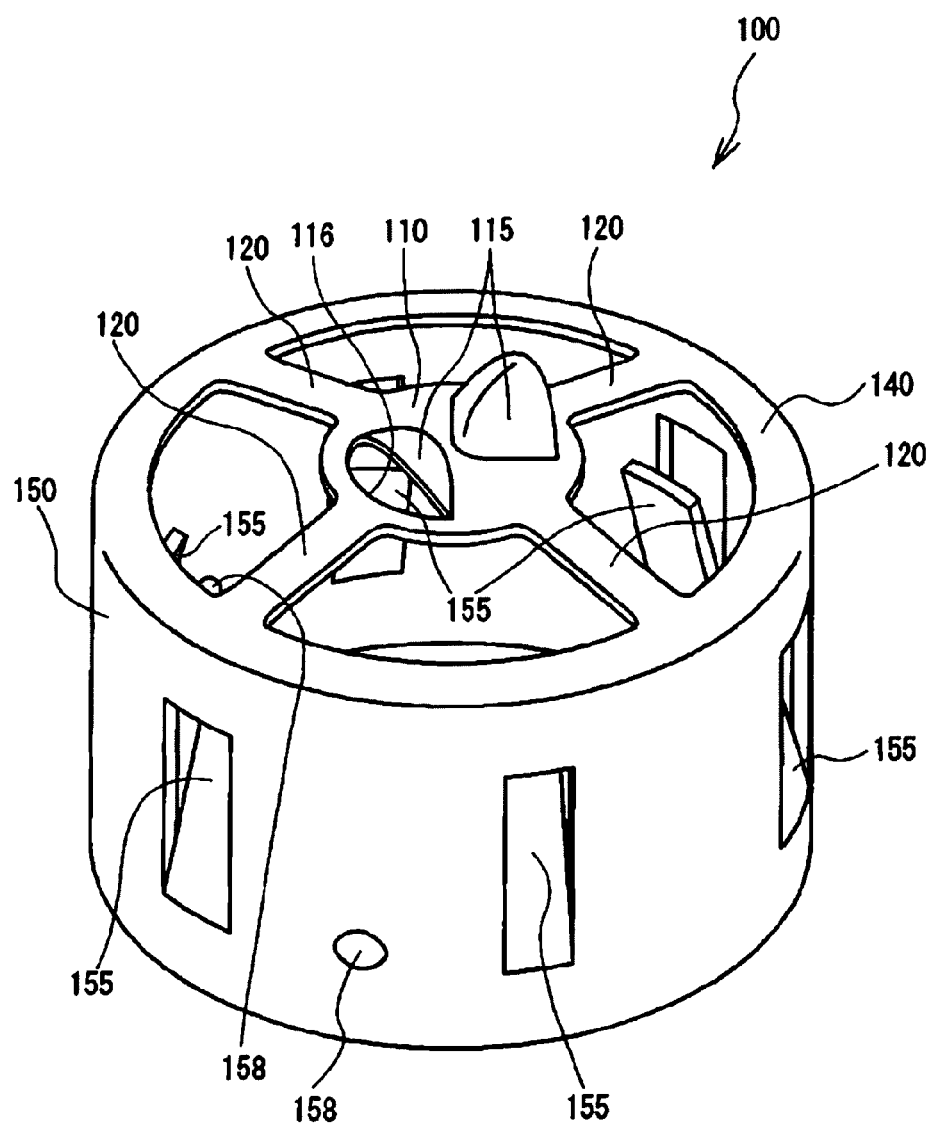
FIG. 14 is a perspective view showing a protection member 100 according to the second embodiment.
Figure 15:
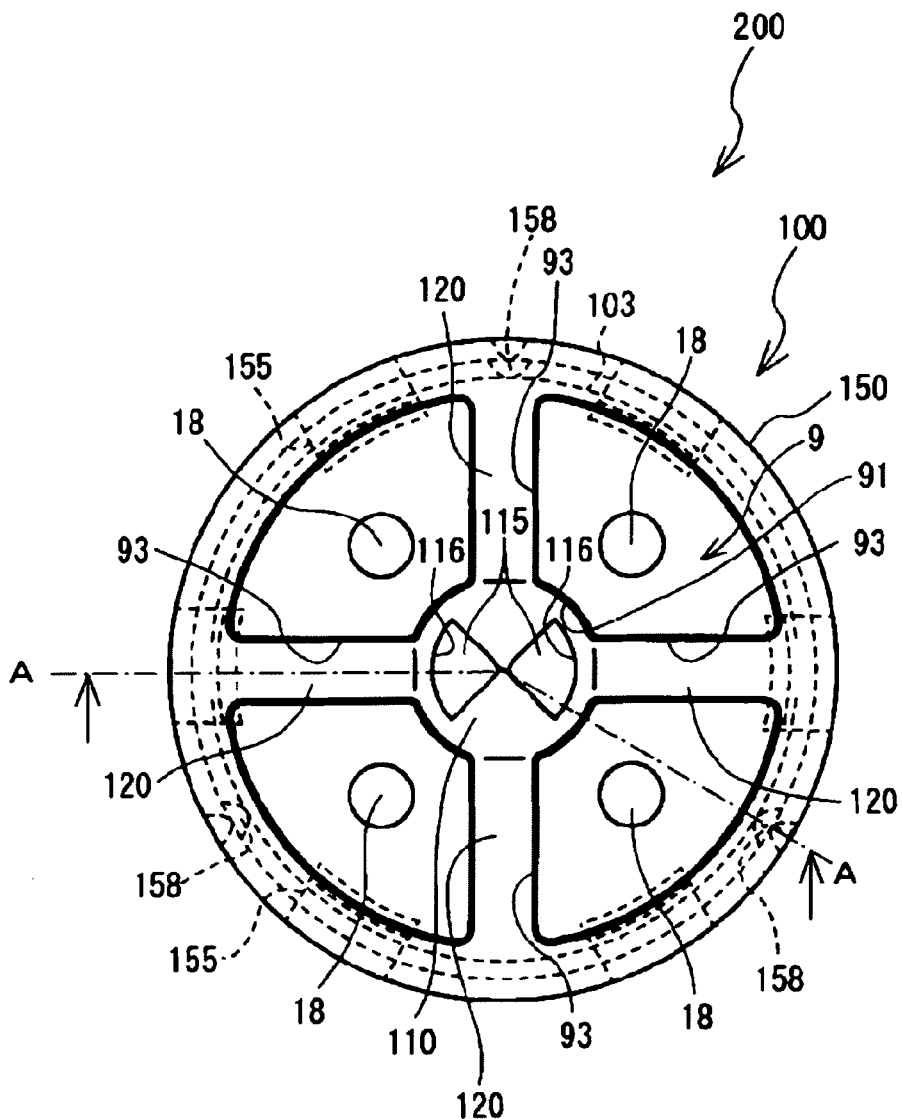
FIG. 15 shows the gas sensor 200, observed from a rear side in the axial O direction (the upper side in FIG. 13)
Figure 16:
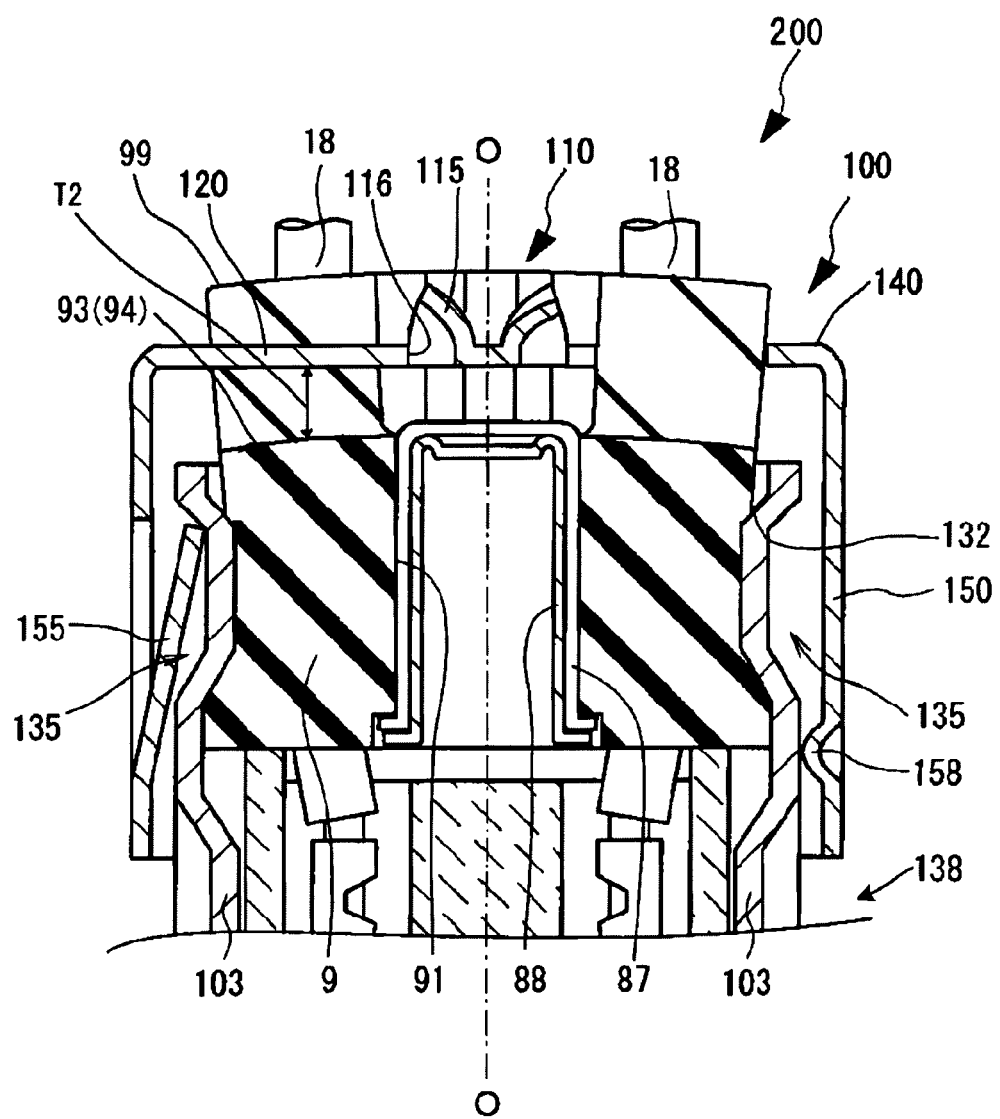
FIG. 16 is a partially enlarged sectional view showing a gas sensor 1, observed in an arrow direction of the bent line A-A represented by a one-dot chain line of FIG. 15.

Next, an example of a gas sensor 200 according to a second embodiment of the invention is described with reference to FIGS. 13 to 16. FIG. 13 is a vertical sectional view showing a structure of the gas sensor 200 according to the second embodiment. FIG. 14 is a perspective view showing a protection member 100 according to the second embodiment. FIG. 15 shows the gas sensor 200, observed from the rear side (the upper side in FIG. 1) in the axial O direction. FIG. 16 is a partially enlarged sectional view showing the rear end of the gas sensor 200, observed from the arrow direction in the bent line A-A represented by the one-dotted chain line of FIG. 15.

Also, the gas sensor 200 of the second embodiment does not include the protection portion 34 and the arm 33 provided to the outer tube 3 as the gas sensor 1 of the first embodiment, but as shown in FIG. 14, the protection unit 100 having a protection portion 110 and an arm 120 is mechanically adhered to an outer tube 103. In addition, the components of the gas sensor 200 other than the protection unit 100 and the outer tube 103 are identical to those of the gas sensor 1. Thus, the outer tube 103 and the protection unit 100 are described here, and the other components are not described or simply described.

As shown in FIG. 13, a front end portion 131 of a cylindrical outer tube 103 made of stainless steel such as SUS304 is engaged to the rear end engagement portion 58 of the metal shell 5. The front end portion 131 is crimped from the outer periphery and adhered to the rear end engagement portion 58 by further performing laser welding around the outer periphery. The outer tube 103 extends toward the rear end along the axial O direction, and surrounds the outer periphery of the rear end portion 66 of the sensor element 6 or the separator 8, which is disposed at a further rear end side, in a radial direction. The outer periphery of the outer tube 103 corresponding to the disposed location of the separator 8 is crimped in a radial direction, and for this reason, the holding bracket 85 is crimped and held in the outer tube 103 while holding the separator 8 therein.

In addition, the grommet 9 made of fluorine-based rubber is fitted into an opening 132 at the rear end of the outer tube 103. The grommet 9 is fixed to the outer tube 103 since the grommet 9 is crimped to the inner side in a radial direction from the outer periphery of the rear end portion 138 of the outer tube 103. In addition, a crimping portion 135 formed by the additional crimping forms a groove shape surrounding the outer periphery of the outer tube 103 in a radial direction with a concave state.

Then, the protection unit 100 for covering the atmosphere communication hole 91 of the grommet 9 and preventing the filter member 87 from being damaged due to external impact such as contact with trees or plants or collision with flying stones may be assembled to the rear end of the outer tube 103. The protection unit 100 is produced by pressing a stainless steel sheet such as SUS into a cap shape as shown in FIG. 14.

The protection unit 100 has a protection portion 110 produced by processing a metal plate into a circular shape, and two carving (dented) portions 115 having openings 116 through the metal plate are formed by depressing the metal plate from the bottom side (the lower side in FIG. 14) in the thickness direction by pressure. Four arms 120 having a plate shape extending outwards in four radial directions are formed around the protection portion 110.

Also, the ends of the arms 120 opposite the protection portion 110 are connected with each other in a circumferential direction by an annular connection unit 140. In addition, the outer periphery of the connection unit 140 extends in the thickness direction of the protection portion 110 to form a cylindrical portion 150 having a cylindrical shape. The cylindrical portion 150 has an inner diameter slightly greater than the outer diameter of the rear end portion 138 of the outer tube 103, and the length of the cylindrical portion 150 in the thickness direction is set so that the cylindrical portion 150 extends further at the rear end of the outer tube 103 toward the front end side than the crimping portion 135. Also, a U-shaped cut portion 155, having a front end in the thickness direction that is connected to the cylindrical portion 150 and having a rear end in the thickness direction that is depressed, is provided to the cylindrical portion 150. Six cut portions 155 are provided at substantially regular intervals in the circumferential direction of the cylindrical portion 150 (six cut portions are just one example, and the number of cut portion may be at least one). In addition, a protruded portion 158 formed by depressing the cylindrical portion 150 to protrude inwards is provided at the front end of the cylindrical portion 150 in the thickness direction. Three protruded portions 158 are provided at substantially regular intervals in the circumferential direction without overlapping the cut portions 155 (FIG. 3 shows two protruded portions). Also, the number of the protruded portions 158 is three as an example, and the number of the protruded portions 158 is preferably at least three, considering that movement of the protection unit 100 should be controlled to the minimum when the protection unit 100 is mounted to the outer tube 103.

As shown in FIGS. 15 and 16, the protection unit 100 configured as above is mounted on the gas sensor 200 by covering the outer tube 103 with the cylindrical portion 150 from the front side in the thickness direction to the rear end 138 of the outer tube 103, disposing the protection portion 110 from the rear end of the filter member 87 to the rear end of the atmosphere communication hole 91, and blocking the atmosphere communication hole 91 with the protection portion 110. At this time, the arms 120 of the protection unit 100 are disposed in the grooves 93 of the grommet 9, respectively, and the cylindrical portion 150 is arranged to surround the outer periphery of the rear end 138 of the outer tube 103. The protruded portions 158 of the cylindrical portion 150 come into contact with the outer periphery of the outer tube 103, where the crimping portion 135 is not formed, and the cylindrical portion 150 is positioned in the radial direction with respect to the outer tube 103 by means of the protruded portions 158. In addition, each cut portion 155 of the cylindrical portion 150 contacts the wall in the groove-type concave portion formed by the crimping portion 135 of the outer tube 103.

In addition, in the protection unit 100, the cylindrical portion 150 is fitted at the rear end of the outer tube 103 from the outside thereof, and the cut portion 155 is supported by the crimping portion 135. At this time, since the cut portion 155 of the protection unit 100 has elasticity, the cut portion 155 may remain engaged with the crimping portion 135 of the outer tube 103 by elastic deformation. Also, since the cylindrical portion 150 is positioned in the radial direction by means of the protruded portion 158, the protection unit 100 may be securely and mechanically fixed to the rear end of the outer tube 103 without movement. In this connection, the protection portion 110 disposed at the rear side of the atmosphere communication hole 91 at a rear end of the filter member 87 disposed in the atmosphere communication hole 91 may maintain protection of the filter member 87 even though an external impact such as contact with trees or plants and collision with flying stones is applied thereto, and also the protection portion 110 may reliably prevent the filter member 87 from being broken. Meanwhile, even though the protection portion 110 covers the atmosphere communication hole 91, the air ventilation of the atmosphere communication hole 91 may be ensured through the protection portion 110 since the opening 116 is formed in the carving portion 115 of the protection portion 110.

Also, if the protection unit 100 is fixed to the outer tube 3, as shown in FIG. 16, the carving portion 115 provided on the protection portion 110 is disposed at a further front end side of the rear end surface 99 of the grommet 9. In other words, the carving portion 115 is disposed in the grommet 9. In this way, the lead wire 18 is not hooked by the edge of the dented portion 115 when being installed. As a result, it is possible to prevent the lead wire 18 from being damaged.

In addition, since the carving portion 115 is disposed in the grommet 9, flying stones do not easily collide with the carving portion 115, and thus the opening 116 formed in the dented portion 115 may favorably maintain air ventilation. In addition, it is possible to prevent the filter member 87 from being broken due to external impact such as contact with trees or plants or collision with flying stones when the protection portion 110 is deformed to expose the filter member 87 to the outside.

Also, since the protection portion 110, the arm 120, and the cylindrical portion 150 having a complex shape are provided as a separate protection unit 100 independently from the outer tube 103, the arm 120 and the protection portion 110 may be easily coupled to the outer tube 103.

In addition, as shown in FIG. 13, while the arms 120 are disposed in the rear end 138 of the outer tube 103 and the grommet 9 is disposed at the rear end side of the separator 8, the rear end surface 99 of the grommet 9 divided into four sections protrudes toward the rear end from the outer tube 103 except for the regions between the four arms 120, and the arms 120 are disposed in the grooves 93 as shown in FIG. 15. Since the arms 120 are disposed in the grooves 93, flying stones do not easily collide with the arms 120. In this way, it is possible to prevent the filter member 87 from being exposed to the outside due to the movement of the protection portion 110, caused by the deformation of the arm 120. As a result, it is possible to prevent the filter member 87 from being broken due to external impact such as contact with trees or plants or collision with flying stones.

In addition, since the arm 120 may be disposed in the groove 93 of the grommet 9, it is possible to prevent the protection portion 110 or the arm 120 from rotating in a circumferential direction of the gas sensor 200. It is also possible to prevent the lead wire 18 from being damaged due to contact with the protection portion 110 or the arm 120.

Also, as shown in FIG. 16, the arm 120 is disposed while forming a gap T2 with the bottom surface 94 of the groove 93. In this way, even though the grommet 9 thermally expands due to the heat received from the exhaust pipe or the exhaust gas or expands at the rear side of the gas sensor 200, the groove 93 of the grommet 9 is not hooked by the arm 120. As a result, the groove 93 of the grommet 9 does not expand with a different ratio from other regions (for example, the four regions that constitute the rear end surface 99), and it is thus possible to suppress the generation of cracks in the groove 93 of the grommet 9.

Also, since a plurality of arms 120 is used, even though one arm 120 is distorted, the other arms 120 lessen the distortion, and thus the protection portion 110 may securely cover the atmosphere communication hole 91 of the grommet 9 from the rear side of the outer tube 103. In addition, in the case where a plurality of arms 120 is used, since the arms 120 are respectively disposed in the plurality of grooves 93 provided in the grommet 9, it is possible to reliably prevent the protection portion 110 or the arms 120 from rotating in a circumferential direction of the gas sensor 200, and it is also possible to prevent the lead wire 18 from being damaged due to contact with the protection portion 110 or the arm 120.

Next, one example of a method for producing the gas sensor 200 is described in the following sequence.

Also, though the method for producing the gas sensor 200 according to the second embodiment is performed using the mounting jig 400 similarly to the method for producing the gas sensor 1 according to the first embodiment, the outer tube 103 is not held by the mounting jig 400, unlike the first embodiment, but the protection unit 100 is held by the mounting jig 400. Hereinafter, the processes identical to those of the method for producing the gas sensor 1 according to the first embodiment are not described in detail here.

First, the sensor element 6 is held to the metal shell 5, and the protector 4 is united thereto by welding, thereby producing an intermediary body.

Meanwhile, core wires of lead wires 18 of the four connection terminals 19 made of conductive plates are fixed by crimping, among which two connection terminals 19 are connected to the electrode 71 of the heater 7. Along with receiving the connection terminals 19 and the heater 7 in the separator 8, the lead wires 18 are inserted into the separator 8 and the grommet 9. Also, the separator 8 and the grommet 9 into which the lead wires 18 are inserted and connected are disposed in the outer tube 103.

After that, the holding bracket 85 is inserted between the outer tube 103 and the separator 8 to crimp the outer tube 103 so that the separator 8 is held by the outer tube 103. Also, the rear end 138 of the outer tube 103 is crimped so that the grommet 9 is fixed to the outer tube 103, and the front end 131 of the outer tube 103 is engaged with the rear end engagement portion 58 of the metal shell 5. Also, the periphery of the front end 131 is crimped, and laser welding is applied thereto.

Then, the holding process, the lead wire holding process, the disposing process, and the shifting process are executed in order. Also, in the method for producing the gas sensor 1 of the first embodiment, the attachment member 400 is integrally held to the outer tube 3 during the holding process, the outer tube 3 integrated with the attachment member 400 is disposed to reach the rear end of the grommet 9 during the disposing process, and the outer tube 3 is pressed in the mounting direction along the axis O during the shifting process.

In contrast, in the method for producing the gas sensor 200 of the second embodiment, the attachment member 400 is integrally held to the protection unit 100 during the holding process, the protection unit 100 integrated with the attachment member 400 is disposed to reach the rear end of the grommet 9 during the disposing process, and the protection unit 100 is pressed in the mounting direction along the axis O during the shifting process. Then, the gas sensor 200 is completely produced.

In addition, the configurations in the above embodiments are just examples, and various modifications can be made thereto.

In addition, though the first and second embodiments illustrate that the number of arms 33 and 120 supporting the protection portion 34 and 110 is four or two, it is also possible for one arm to support the protection portion. The number of arms may also be three, five, or more. Also, the number of grooves 93 of the grommet 9 may also be increased or decreased depending on the number of arms, and the number of grooves 93 may be greater than the number of arms.

In addition, though the protection unit 100 is mechanically united to the outer tube 103 in the second embodiment, the invention is not limited thereto, and it is possible to fix the protection unit 100 to the outer tube 103 by crimping the protection unit 100 in accordance with the crimping unit 135 of the outer tube 103.

Also, although the sensor element 6 is configured as a lower cylinder in the gas sensors 1 and 200 according to the first and second embodiments, the invention is not limited thereto, and the sensor element 6 may have a plate shape.

It should further be apparent to those skilled in the art that various changes in form and detail of the invention as shown and described above may be made. It is intended that such changes be included within the spirit and scope of the claims appended hereto.

This application claims priority from Japanese Patent Application No. 2010-085762, filed on Apr. 2, 2010, the disclosure of which is incorporated herein by reference in its entirety.

What is claimed is:

1. A gas sensor, comprising:
a sensor element extending in an axial direction and having a detection portion for detecting gas to be detected at a front end thereof;
a metal shell that surrounds a periphery of the sensor element in a radial direction while allowing the detection portion to protrude from a front end thereof;
a cylindrical outer tube disposed at a rear side of the metal shell and having a front end fixed to the metal shell; and
a seal member disposed in the outer tube, the seal member including:
a lead wire insert hole into which a lead wire for extracting a detection signal of the detector is inserted, the lead wire insert hole extending in an axial direction thereof, and
an atmosphere communication hole allowing atmospheric communication between an inside and an outside of the outer tube through a filter member having air ventilation and waterproofing properties, the atmosphere communication hole extending in an axial direction thereof,
wherein the gas sensor further includes:
a protection portion that protects the filter member by covering the atmosphere communication hole of the seal member from a rear end of the gas sensor in the axial direction, the protection portion having a protrusion which protrudes toward a rear side of the gas sensor, and has an opening smaller than an opening of the atmosphere communication hole, and
wherein the protrusion is disposed entirely to the front of a rear end surface of the seal member.

2. The gas sensor according to claim 1, further comprising an arm extending from the protection portion in the radial direction, wherein the arm and the protection portion are integrally formed with the outer tube.

3. The gas sensor according to claim 2, wherein the seal member is held in the outer tube by crimping the outer tube to an inner side thereof in the radial direction.

4. The gas sensor according to claim 1, wherein the gas sensor includes a protection unit having an arm extending from the protection portion in the radial direction and a cylindrical portion connected to the arm and covering the periphery of the outer tube, and
wherein the cylindrical portion is mechanically fixed to the outer tube so that the protection unit is coupled to the outer tube.

5. The gas sensor according to claim 2,
wherein the seal member has a groove extending outwards in a radial direction at a rear end-facing surface of the seal member from the atmosphere communication hole while circumventing the lead wire insert hole, the groove having a cutout toward the front end of the seal member, and
wherein the arm is at least partially disposed in the groove of the seal member.

6. The gas sensor according to claim 5,
wherein a plurality of grooves extends outwards in the radial direction at the rear end surface of the seal member from the atmosphere communication hole while circumventing the lead wire insert hole, and
wherein a plurality of arms is disposed in the grooves of the seal member.

* * * * *